US 12,005,147 B2

(12) United States Patent
Hong et al.

(10) Patent No.: US 12,005,147 B2
(45) Date of Patent: Jun. 11, 2024

(54) STERILIZATION CASE

(71) Applicant: LG Electronics Inc., Seoul (KR)

(72) Inventors: Seongkyeol Hong, Seoul (KR); Hyungho Park, Seoul (KR); Wansu Youn, Seoul (KR); Hoon Kim, Seoul (KR); Jieun Choi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 488 days.

(21) Appl. No.: 17/244,683

(22) Filed: Apr. 29, 2021

(65) Prior Publication Data

US 2022/0062469 A1 Mar. 3, 2022

(30) Foreign Application Priority Data

Aug. 28, 2020 (KR) .................. 10-2020-0109160

(51) Int. Cl.
*A61L 2/10* (2006.01)
*A61L 2/26* (2006.01)
*A62B 18/02* (2006.01)

(52) U.S. Cl.
CPC ........ *A61L 2/10* (2013.01); *A61L 2/26* (2013.01); *A61L 2202/11* (2013.01); *A61L 2202/121* (2013.01); *A61L 2202/122* (2013.01); *A61L 2202/14* (2013.01); *A62B 18/025* (2013.01)

(58) Field of Classification Search
CPC .......... A61L 2/10; A61L 2/26; A61L 2202/11; A61L 2202/121; A61L 2202/122; A61L 2202/14; A61L 2202/16; A61L 2202/20; A62B 18/025; A62B 18/02; A62B 18/08

USPC .................................. 250/455.11, 453.11
See application file for complete search history.

(56) References Cited

U.S. PATENT DOCUMENTS

| 4,546,793 | A  | 10/1985 | Stupecky     |
| 4,646,732 | A  | 3/1987  | Chien        |
| 5,062,421 | A  | 11/1991 | Burns et al. |
| 5,372,130 | A  | 12/1994 | Stern et al. |
| 5,782,234 | A  | 7/1998  | Bates        |
| 6,213,119 | B1 | 4/2001  | Brydon       |

(Continued)

FOREIGN PATENT DOCUMENTS

| CN | 1455270   | 11/2003 |
| CN | 103505788 | 1/2014  |

(Continued)

OTHER PUBLICATIONS

Office Action in Japanese Appln. No. 2020-204668, dated Feb. 7, 2022, 12 pages (with English translation).

(Continued)

*Primary Examiner* — Jason L McCormack
(74) *Attorney, Agent, or Firm* — Fish & Richardson P.C.

(57) ABSTRACT

A sterilization case includes a case body having a seating surface configured to seat an object to be sterilized, a case cover that is coupled to the case body, the case cover and the case body defining an accommodation space that is configured to accommodate therein the object to be sterilized, a sterilization module that is provided at the case body and configured to sterilize the object to be sterilized, and a reflective pattern provided at an inner surface of the case cover and configured to reflect ultraviolet light emitted from the sterilization module onto a surface of the object to be sterilized.

19 Claims, 16 Drawing Sheets

(56) References Cited

U.S. PATENT DOCUMENTS

| | | | |
|---|---|---|---|
| 6,543,450 B1 | 4/2003 | Flynn | |
| 8,667,959 B2 | 3/2014 | Tilley et al. | |
| 10,226,542 B2 | 3/2019 | Messina et al. | |
| 10,342,999 B2 | 7/2019 | Song | |
| 10,661,104 B2 | 5/2020 | Morgan et al. | |
| 11,241,594 B2 | 2/2022 | Szasz et al. | |
| 2003/0052279 A1* | 3/2003 | Kikuchi | G03F 7/2008 250/455.11 |
| 2003/0066257 A1 | 4/2003 | Shovlin | |
| 2003/0066527 A1 | 4/2003 | Chen | |
| 2005/0145249 A1 | 7/2005 | Solyntjes et al. | |
| 2006/0076012 A1 | 4/2006 | Tanizawa et al. | |
| 2007/0125385 A1 | 6/2007 | Ho et al. | |
| 2009/0320847 A1 | 12/2009 | Bozanic et al. | |
| 2010/0101575 A1 | 4/2010 | Fedorko et al. | |
| 2010/0224190 A1 | 9/2010 | Tilley et al. | |
| 2010/0313892 A1 | 12/2010 | Shigematsu et al. | |
| 2010/0329924 A1* | 12/2010 | Harris | A61L 2/202 422/291 |
| 2011/0126713 A1 | 6/2011 | Legare et al. | |
| 2014/0216475 A1 | 8/2014 | Blomberg et al. | |
| 2014/0360501 A1 | 12/2014 | Guiducci et al. | |
| 2015/0034080 A1 | 2/2015 | Furuichi et al. | |
| 2015/0047642 A1 | 2/2015 | Tucker et al. | |
| 2015/0136142 A1 | 5/2015 | Blomberg | |
| 2015/0151143 A1 | 6/2015 | Langford | |
| 2015/0202473 A1 | 7/2015 | Curran et al. | |
| 2015/0217144 A1 | 8/2015 | Skov et al. | |
| 2015/0217146 A1 | 8/2015 | Skov et al. | |
| 2015/0250915 A1* | 9/2015 | Pugh | A45C 11/005 250/455.11 |
| 2015/0289598 A1 | 10/2015 | Hsiung | |
| 2015/0306324 A1 | 10/2015 | Ayon et al. | |
| 2015/0362478 A1 | 12/2015 | Phillips | |
| 2016/0001111 A1 | 1/2016 | Morgan et al. | |
| 2016/0022944 A1 | 1/2016 | Chodkowski et al. | |
| 2016/0030778 A1 | 2/2016 | Skov et al. | |
| 2016/0030779 A1 | 2/2016 | Twu et al. | |
| 2016/0074604 A1 | 3/2016 | Bronner et al. | |
| 2016/0236016 A1 | 8/2016 | Ono et al. | |
| 2016/0279450 A1 | 9/2016 | Goldstein et al. | |
| 2017/0136271 A1 | 5/2017 | Munster | |
| 2017/0157353 A1 | 6/2017 | Olsen et al. | |
| 2018/0078798 A1 | 3/2018 | Fabian et al. | |
| 2018/0177965 A1 | 6/2018 | Patel | |
| 2018/0185677 A1 | 7/2018 | Curran et al. | |
| 2018/0236275 A1 | 8/2018 | Song et al. | |
| 2018/0318457 A1* | 11/2018 | Lucio | A61L 2/0047 |
| 2019/0009114 A1 | 1/2019 | Han | |
| 2019/0113501 A1 | 4/2019 | Jameson et al. | |
| 2019/0160249 A1 | 5/2019 | Rose et al. | |
| 2019/0175962 A1 | 6/2019 | Su et al. | |
| 2019/0275357 A1 | 9/2019 | Palmer, Jr. et al. | |
| 2020/0008539 A1 | 1/2020 | Kolasa | |
| 2020/0038614 A1 | 2/2020 | Duff et al. | |
| 2020/0086071 A1 | 3/2020 | Lin et al. | |
| 2020/0087031 A1 | 3/2020 | Yoo et al. | |
| 2020/0129650 A1 | 4/2020 | Kim et al. | |
| 2020/0155877 A1 | 5/2020 | Key et al. | |
| 2021/0228920 A1 | 7/2021 | Arigue et al. | |
| 2021/0337891 A1 | 11/2021 | Shah et al. | |
| 2021/0378325 A1 | 12/2021 | Mun et al. | |
| 2021/0379412 A1 | 12/2021 | Lee et al. | |
| 2021/0379418 A1 | 12/2021 | Kim et al. | |
| 2021/0402222 A1 | 12/2021 | Kwon et al. | |
| 2022/0016449 A1 | 1/2022 | Choi et al. | |

FOREIGN PATENT DOCUMENTS

| | | |
|---|---|---|
| CN | 103751919 | 4/2014 |
| CN | 104162236 | 11/2014 |
| CN | 203943119 | 11/2014 |
| CN | 104826247 | 8/2015 |
| CN | 204637356 | 9/2015 |
| CN | 105126219 | 12/2015 |
| CN | 105167366 | 12/2015 |
| CN | 105476118 | 4/2016 |
| CN | 105495776 | 4/2016 |
| CN | 105641821 | 6/2016 |
| CN | 205285072 | 6/2016 |
| CN | 106039607 | 10/2016 |
| CN | 106235464 | 12/2016 |
| CN | 106253937 | 12/2016 |
| CN | 106730464 | 5/2017 |
| CN | 106847663 | 6/2017 |
| CN | 107149182 | 9/2017 |
| CN | 206459266 | 9/2017 |
| CN | 107224687 | 10/2017 |
| CN | 206577264 | 10/2017 |
| CN | 107308564 | 11/2017 |
| CN | 107405508 | 11/2017 |
| CN | 107735148 | 2/2018 |
| CN | 206995630 | 2/2018 |
| CN | 207011751 | 2/2018 |
| CN | 207040968 | 2/2018 |
| CN | 207041756 | 2/2018 |
| CN | 207152901 | 3/2018 |
| CN | 207604526 | 7/2018 |
| CN | 207721249 | 8/2018 |
| CN | 207836817 | 9/2018 |
| CN | 108635689 | 10/2018 |
| CN | 208145256 | 11/2018 |
| CN | 109078277 | 12/2018 |
| CN | 208403333 | 1/2019 |
| CN | 208611622 | 3/2019 |
| CN | 208694061 | 4/2019 |
| CN | 109924568 | 6/2019 |
| CN | 111135492 | 5/2020 |
| CN | 111565763 | 8/2020 |
| EP | 0558147 | 9/1993 |
| EP | 0621056 | 10/1994 |
| EP | 2913083 | 9/2015 |
| EP | 3446755 | 2/2019 |
| EP | 3446756 | 2/2019 |
| GB | 1155046 | 6/1969 |
| JP | H05137808 | 6/1993 |
| JP | 3039303 | 7/1997 |
| JP | H09225012 | 9/1997 |
| JP | 10066817 | 3/1998 |
| JP | H10165527 | 6/1998 |
| JP | 3077655 | 5/2001 |
| JP | 2003322712 | 11/2003 |
| JP | 2004364177 | 12/2004 |
| JP | 3117209 U | 1/2006 |
| JP | 2007236600 | 9/2007 |
| JP | 2011078604 | 4/2011 |
| JP | 2011078678 | 4/2011 |
| JP | 2011115449 | 6/2011 |
| JP | 2012-075793 | 4/2012 |
| JP | 2013127129 | 6/2013 |
| JP | 3196218 | 2/2015 |
| JP | 2015093036 | 5/2015 |
| JP | 2015-524337 | 8/2015 |
| JP | 2015527130 | 9/2015 |
| JP | 2016087376 | 5/2016 |
| JP | 2018000982 | 1/2018 |
| JP | 2018033905 | 3/2018 |
| JP | 2018089158 | 6/2018 |
| JP | 2018-146805 | 9/2018 |
| JP | 2019501721 | 1/2019 |
| KR | 10-1989-0000137 | 3/1989 |
| KR | 10-1995-0008732 | 8/1995 |
| KR | 20050061384 | 6/2005 |
| KR | 20100081991 | 7/2010 |
| KR | 20-2010-0009804 | 10/2010 |
| KR | 1020110067854 | 6/2011 |
| KR | 20120051735 | 5/2012 |
| KR | 200461294 | 7/2012 |
| KR | 101228403 | 1/2013 |
| KR | 101536265 | 7/2015 |
| KR | 101554664 | 9/2015 |
| KR | 101619487 | 5/2016 |
| KR | 20160062808 | 6/2016 |

(56) References Cited

FOREIGN PATENT DOCUMENTS

| | | |
|---|---|---|
| KR | 20160129562 | 11/2016 |
| KR | 20160132159 | 11/2016 |
| KR | 101733470 | 4/2017 |
| KR | 20170111132 | 10/2017 |
| KR | 20170126163 | 11/2017 |
| KR | 20180009326 | 1/2018 |
| KR | 10-2018-0012496 | 2/2018 |
| KR | 101827016 | 2/2018 |
| KR | 1020180027561 | 3/2018 |
| KR | 101849610 | 4/2018 |
| KR | 20180043234 | 4/2018 |
| KR | 20180045934 | 5/2018 |
| KR | 20180064284 | 6/2018 |
| KR | 20180091698 | 8/2018 |
| KR | 20180128040 | 11/2018 |
| KR | 10-2018-0130658 | 12/2018 |
| KR | 101925388 | 12/2018 |
| KR | 1020180135840 | 12/2018 |
| KR | 10-1942785 | 1/2019 |
| KR | 20190033299 | 3/2019 |
| KR | 1020190033299 | 3/2019 |
| KR | 10-2019-0053757 | 5/2019 |
| KR | 10-2019- 0022668 | 6/2019 |
| KR | 102002878 | 7/2019 |
| KR | 1020190089188 | 7/2019 |
| KR | 1020190096496 | 8/2019 |
| KR | 102023974 | 9/2019 |
| KR | 10-2019-0119804 | 10/2019 |
| KR | 101997813 | 10/2019 |
| KR | 102065360 | 2/2020 |
| KR | 1020200033495 | 3/2020 |
| KR | 102110687 | 5/2020 |
| KR | 20200048502 | 5/2020 |
| KR | 1020200048502 | 5/2020 |
| KR | 1020200049490 | 5/2020 |
| KR | 1020200079925 | 7/2020 |
| TW | 201201879 | 1/2012 |
| TW | M555232 | 2/2018 |
| TW | 201904614 | 2/2019 |
| WO | WO 1996/22124 | 7/1996 |
| WO | WO2009067583 | 5/2009 |
| WO | WO2010070495 | 6/2010 |
| WO | WO2014020469 | 2/2014 |
| WO | WO 2016/072868 | 5/2016 |
| WO | WO2016157159 | 10/2016 |
| WO | WO20170004313 | 1/2017 |
| WO | WO2017116174 | 7/2017 |
| WO | WO2018036902 | 3/2018 |
| WO | WO2018147941 | 8/2018 |
| WO | WO 2019/059699 | 3/2019 |
| WO | WO2019194950 | 10/2019 |
| WO | WO2020055106 | 3/2020 |
| WO | WO2020094850 | 5/2020 |

OTHER PUBLICATIONS

Office Action in Korean Appln. No. 10-2020-0080437, dated Feb. 21, 2022, 13 pages (with English translation).
Office Action in Korean Appln. No. 10-2020-0068421, dated Jan. 23, 2022, 12 pages (with English translation).
Extended European Search Report in European Appln. No. 21169778. 4, dated Oct. 15, 2021, 5 pages.
Extended European Search Report in European Appln. No. 21169793. 3, dated Oct. 15, 2021, 4 pages.
Extended European Search Report in European Appln. No. 21169796. 6, dated Oct. 18, 2021, 4 pages.
Extended European Search Report in European Appln. No. 21169813. 9, dated Oct. 20, 2021, 4 pages.
Extended European Search Report in European Appln. No. 21169817. 0, dated Oct. 14, 2021, 4 pages.
Extended European Search Report in European Appln. No. 21170476. 2, dated Oct. 13, 2021, 4 pages.
Extended European Search Report in European Appln. No. 21170861. 5, dated Oct. 25, 2021, 4 pages.
Notice of Allowance in Japanese Appln. No. 2020-204668, dated Aug. 16, 2022, 5 pages (with English translation).
Office Action in Chinese Appln. No. 202110552518.6, dated Jul. 4, 2022, 18 pages (with English translation).
Decision to Grant a Patent in Japanese Appln. No. 2021-043251, dated Oct. 25, 2022, 5 pages (with English translation).
Office Action in European Appln. No. 20217533.7, dated Nov. 23, 2022, 5 pages.
Office Action in European Appln. No. 21182279.6, dated Oct. 17, 2022, 2 pages.
Office Action in Taiwanese Appln. No. 110117972, dated Oct. 7, 2022, 14 pages (with English translation).
Office Action in U.S. Appl. No. 17/170,035, dated Sep. 29, 2022, 19 pages.
Written Decision on Registration in Korean Appln. No. 10-2020-0080437, dated Oct. 22, 2022, 11 pages (with English translation).
Notice of Allowance in Korean Appln. No. 10-2020-0068413, dated May 31, 2022, 4 pages (with English translation).
Notice of Allowance in Korean Appln. No. 10-2020-0080087, dated Jun. 30, 2022, 5 pages (with English translation).
Office Action in Chinese Appln. No. 202011328161.5, dated Apr. 2, 2022, 15 pages (with English translation).
Office Action in Chinese Appln. No. 202110046911.8, dated Apr. 15, 2022, 12 pages (with English translation).
Office Action in Chinese Appln. No. 202110382635.2, dated Apr. 20, 2022, 12 pages (with English translation).
Office Action in Chinese Appln. No. 202110383659.X, dated Apr. 18, 2022, 13 pages (with English translation).
Office Action in Chinese Appln. No. 202110404827.9, dated Apr. 19, 2022, 13 pages (with English translation).
Office Action in Indian Appln. No. 202114011936, dated May 5, 2022, 5 pages.
Office Action in Japanese Appln. No. 2021-043251, dated May 10, 2022, 6 pages (with English translation).
Office Action in Japanese Appln. No. 2021-073811, dated May 10, 2022, 6 pages (with English translation).
Office Action in Japanese Appln. No. 2021-074825, dated Apr. 19, 2022, 6 pages (with English translation).
Office Action in Japanese Appln. No. 2021-090930, dated Jun. 14, 2022, 10 pages (with English translation).
Extended European Search Report in European Appln. No. 21169773. 5, dated Sep. 24, 2021, 4 pages.
Extended European Search Report in European Appln. No. 21169777. 6, dated Sep. 24, 2021, 5 pages.
Office Action in Taiwanese Appln. No. 11120021940, dated Dec. 20, 2020, 11 pages (with English translation).
Notice of Allowance in Korean Appln. No. 10-2020-0068407, dated Nov. 29, 2021, 4 pages (with English translation).
Office Action in Korean Appln. No. 10-2020-0068400, dated Dec. 27, 2021, 13 pages (with English translation).
Office Action in Korean Appln. No. 10-2020-0068412, dated Dec. 27, 2021, 15 pages (with English translation).
Office Action in Korean Appln. No. 10-2020-0080417, dated Dec. 28, 2021, 13 pages (with English translation).
Office Action in Korean Appln. No. 10-2020-0089132, dated Dec. 28, 2021, 13 pages (with English translation).
Office Action in Korean Appln. No. 10-2020-0068413, dated Nov. 17, 2021, 13 pages (with English translation).
Office Action in Korean Appln. No. 10-2020-0080087, dated Nov. 30, 2021, 15 pages (with English translation).
Office Action in Indian Appln. No. 202114007027, dated Jan. 5, 2022, 6 pages.
Office Action in Indian Appln. No. 202114003123, dated Jan. 6, 2022, 5 pages.
Office Action in Indian Appln. No. 202114008985, dated Jan. 12, 2022, 5 pages.
Office Action in Indian Appln. No. 202114003125, dated Jan. 13, 2022, 5 pages.
Office Action in Indian Appln. No. 202114007372, dated Jan. 24, 2022, 6 pages.
Extended European Search Report in European Appln. No. 20217533. 7, dated Jun. 8, 2021, 5 pages.

(56) References Cited

OTHER PUBLICATIONS

Korean Office Action in Korean Appln. No. 2020-0068404, dated Apr. 5, 2021, 11 pages (with English translation).
Korean Office Action in Korean Appln. No. 2020-0068407, dated Apr. 5, 2021, 11 pages (with English translation).
Korean Office Action in Korean Appln. No. 2020-0068611, dated Apr. 5, 2021, 11 pages (with English translation).
Korean Office Action in Korean Appln. No. 2020-0109160, dated Feb. 11, 2021, 21 pages (with English translation).
Office Action in Chinese Appln. No. 202011403700.7, dated May 4, 2023, 18 pages (with English translation).
Office Action in Chinese Appln. No. 202110096186.5, dated Jun. 3, 2023, 16 pages (with English translation).
Office Action in United States U.S. Appl. No. 17/230,206, dated Jun. 22, 2023, 18 pages.
Office Action in United States U.S. Appl. No. 17/231,472, dated Jun. 23, 2023, 23 pages.
Extended European Search Report in European Appln. No. 20217535.2, dated Jun. 22, 2021, 4 pages.
Extended European Search Report in European Appln. No. 20217537.8, dated Jun. 22, 2021, 4 pages.
Office Action in Korean Appln. No. 10-2020-0068404, dated Jun. 30, 2021, 12 pages (with English translation).
Office Action in Korean Appln. No. 10-2020-0068611, dated Jun. 30, 2021, 12 pages (with English translation).
Office Action in Taiwanese Appln. No. 109146705, dated Jul. 7, 2021, 19 pages (with English translation).
Office Action in Taiwanese Appln. No. 110102539, dated Jul. 12, 2021, 10 pages (with English translation).
Office Action in Taiwanese Appln. No. 110102540, dated Jul. 12, 2021, 19 pages (with English translation).
Office Action in Taiwanese Appln. No. 110105039, dated Jul. 12, 2021, 15 pages (with English translation).
Korean Office Action in Korean Appln. No. 10-2020-0068402, dated Oct. 15, 2020, 20 pages (with English translation).
Office Action in U.S. Appl. No. 17/178,103, dated Jun. 30, 2023, 30 pages.
Office Action in Chinese Appln. No. 202011089763, dated Feb. 11, 2023, 18 pages (with English translation).
Office Action in Chinese Appln. No. 202011328031, dated Feb. 15, 2023, 18 pages (with English translation).
Office Action in Chinese Appln. No. 202110184702, dated Mar. 18, 2023, 23 pages (with English translation).
Office Action in Korean Appln. No. 20210129533, dated Mar. 28, 2023, 18 pages (with English translation).
Office Action in Korean Appln. No. 20220126062, dated Mar. 23, 2023, 23 pages (with English translation).
Office Action in U.S. Appl. No. 17/170,035, dated Feb. 8, 2023, 8 pages.
Chen et al., "Algorithm description for Versatile Video Coding and Test Model 3 (VTM 3)," JVET-L1002-vl, Joint Video Experts Team (JVET) of ITU-T SG 16 WP 3 and ISO/IEC JTC I/SC 29/WG 11, 12th Meeting: Macao, CN, Oct. 3-12, 2018, 37 pages.
Li et al., "CE3-6.2.1: Extended MPM list," JVET-L0165-v1, Presented at Joint Video Experts Team (JVET) of ITU-T SG 16 WP 3 and 1S0/IEC JTC 1/SC 29/WG 11, 12th Meeting: Macao, CN, Oct. 3-12, 2018, 6 pages.
Partial Supplementary European Search Report in European Appln. No. 20738225.0, dated Feb. 14, 2022, 15 pages.
Tian et al., "Adaptive intra mode decision for HEVC based on texture characteristics and multiple reference lines," Multimedia Tools and Applications, Jan. 2019, 78(1):289-310.
Notice of Allowance in U.S. Appl. No. 17/178,103, dated Nov. 3, 2023, 12 pages.
Office Action in Korean Appln. No. 10-2022-0126062, dated Sep. 26, 2023, 8 pages (with English translation).
Office Action in U.S. Appl. No. 17/230,206, dated Oct. 12, 2023, 19 pages.
Office Action in U.S. Appl. No. 17/231,472, dated Oct. 23, 2023, 19 pages.
Office Action in U.S. Appl. No. 17/112,500, dated Nov. 28, 2023, 14 pages.
Notice of Allowance in U.S. Appl. No. 17/174,766, mailed on Dec. 5, 2023, 12 pages.
Office Action in Chinese Appln. No.202110096186.5, mailed on Feb. 9, 2024, 7 pages (with English translation).
Office Action in U.S. Appl. No. 17/121,056, mailed on Dec. 21, 2023, 10 pages.
Office Action in U.S. Appl. No. 17/121,115, mailed on Dec. 20, 2023, 11 pages.
Office Action in U.S. Appl. No. 17/231,462, mailed on Dec. 28, 2023, 17 pages.
Office Action in U.S. Appl. No. 17/231,472, mailed on Feb. 27, 2024, 20 pages.

* cited by examiner

STERILIZATION CASE

CROSS-REFERENCE TO RELATED APPLICATIONS

The present application claims the benefits of priority to Korean Patent Application No. 10-2020-0109160, filed on Aug. 28, 2020, the disclosure of which is incorporated herein by reference in its entirety.

TECHNICAL FIELD

The present disclosure relates to an ultraviolet sterilization case.

BACKGROUND

An ultraviolet sterilization case may be defined as a device used for killing harmful bacteria existing on a surface of an object, by irradiating ultraviolet light onto the object to be sterilized wherein the object to be sterilized is placed therein.

For example, a conventional sterilizer can include a lower case in which a UV LED is installed on an inner circumferential surface thereof, an upper case rotatably coupled to the lower case, a cosmetic tool holder horizontally disposed above the UV LED in the lower case to support cosmetic tools, and a reflector horizontally disposed under the UV LED in the lower case.

The cosmetic tool holder is typically made of a transparent material and the reflector is formed in an uneven or irregular structure, a hologram pattern or grating pattern capable of adjusting a diffraction angle according to the wavelength of reflected LED light. In addition, ultraviolet rays irradiated onto the reflector are diffusely reflected onto the cosmetic tool such that the lower surface of the cosmetic tool is sterilized.

However, in the conventional sterilizer for the cosmetic tool, since ultraviolet rays are irradiated onto only the lower surface of the object to be sterilized, it can be difficult to sterilize the upper surface of the object to be sterilized.

In addition, since the reflector located under the object to be sterilized is designed to cause diffuse reflection in the irregular pattern structure, light uniformity decreases as the distance from a light source increases. When light uniformity decreases, the sterilization effect can significantly decrease in a portion of the object to the sterilized, which is far from the light source, and discoloration can occur due to exposure to ultraviolet rays in a portion of the object to be sterilized, which is close to the light source.

SUMMARY

The present application describes a sterilization case that can stably mount an object to be sterilized (e.g., a mask, a portable terminal, etc.) and uniformly sterilize the entire surface of the object to be sterilized.

The present application also describes a sterilization case that can shorten sterilization time by efficiently sterilizing a mask and a portable terminal.

The present application further describes a sterilization case that can improve sterilization performance and minimize deterioration due to excessive exposure to ultraviolet rays, by improving light uniformity of ultraviolet rays irradiated onto surfaces of a mask and a portable terminal.

The present application further describes a sterilization case in which ventilation of an inside of a case is facilitated, so that drying is quick and heat dissipation performance of internal electronic parts is improved.

According to one aspect of the subject matter described in this application, a sterilization case includes a case body having a seating surface configured to seat an object to be sterilized, a case cover that is coupled to the case body, the case cover and the case body defining an accommodation space that is configured to accommodate therein the object to be sterilized, a sterilization module that is provided at the case body and configured to sterilize the object to be sterilized, and a reflective pattern provided at an inner surface of the case cover and configured to reflect ultraviolet light emitted from the sterilization module onto a surface of the object to be sterilized.

Implementations according to this aspect can include one or more of the following features. For example, the reflective pattern can include a lattice pattern or an embossed pattern formed by a plurality of protrusions protruding from the inner surface of the case cover.

In some implementations, a density of the plurality of protrusions defining the reflective pattern can increase from an edge of the case cover to a center of the case cover. In some examples, each of the plurality of protrusions can have a transverse section of a circular or a polygonal shape.

In some implementations, the case cover can include an outer cover having a semicircular or hemispherical shape, and an inner cover coupled to an inner side of the outer cover. The reflective pattern can be provided at a bottom surface of the inner cover. In some examples, at least a portion of the inner cover can be coated or plated.

In some implementations, the sterilization module can include a first sterilization module disposed on a central portion of the seating surface, a second sterilization module disposed on one edge of the seating surface, and a third sterilization module disposed on another edge of the seating surface.

In some examples, the first sterilization module can be configured to irradiate ultraviolet light toward a bottom surface of the object to be sterilized, and the second sterilization module and the third sterilization module can be configured to irradiate ultraviolet light toward a side surface of the object to be sterilized and the inner surface of the case cover.

In some implementations, each of the first sterilization module, the second sterilization module, and the third sterilization module can be spaced apart from the bottom surface of the outer case at a same height. In some implementations, the first sterilization module, the second sterilization module, and the third sterilization module can be arranged along a length direction of the case body.

In some implementations, the case body can include an outer case disposed on a support surface, and an inner case coupled to an inner side of the outer case to define the seating surface. The seating surface can be disposed on an upper surface of the inner case. In some examples, the outer case and the inner case define a separation space that is configured to accommodate the sterilization module.

In some implementations, the seating surface can include a first recessed part recessed downward from the upper surface of the inner case by a predetermined depth and having an opening therein, a pair of second recessed parts recessed downward from both ends of the first recessed part by a predetermined depth, and a pair of third recessed parts respectively recessed downward from both ends of the pair of second recessed parts by a predetermined depth.

In some implementations, the sterilization case can further include a ventilation grill provided at the opening. The ventilation grill can include a flat bottom portion, and a grill portion extending from an edge of the flat bottom portion to be inclined or stepped upward defining an air passage hole therein. In some examples, an upper end of the grill portion can be coupled to an edge of the opening.

In some implementations, the first sterilization module can include a board provided at the separation space and in contact with a bottom surface of the flat bottom portion, and a pair of light emitting diode (LED) devices disposed on the board and spaced apart from each other in a length direction of the case body. A pair of insertion holes that accommodate the pair of LED devices can be defined in the flat bottom portion.

In some implementations, a ventilation hole, configured to pass air, can be defined in the outer case. The ventilation hole can be disposed below the ventilation grill.

In some implementations, the object to be sterilized can include a mask device. The mask device can include a mask body configured to cover a person's face, a mask body cover coupled to a front surface of the mask body, and a sealing part having a closed loop shape that is coupled to a rear surface of the mask body and configured to be in close contact with the person's face to define a breathing space therein. In some examples, both ends of the mask body cover can be seated on the pair of second recessed parts.

In some implementations, the first recessed part can be disposed below the sealing part. In some implementations, the second sterilization module and the third sterilization module can be provided at the pair of third recessed parts, respectively. Each of the second sterilization module and the third sterilization module can include a board provided at the separation space and in close contact with a bottom surface of the inner case defining the pair of third recessed parts, and a pair of LED devices disposed on the board and spaced apart from each other in a width direction of the case body. In some examples, a pair of insertion holes that accommodate the pair of LED devices can be defined in the pair of third recessed parts.

In some implementations, the sterilization case can further include a main control board accommodated in the separation space and disposed to surround the ventilation grill.

DETAILED DESCRIPTION

Hereinafter, some implementations of the present disclosure will be described in detail with reference to the drawings.

Figure 1:
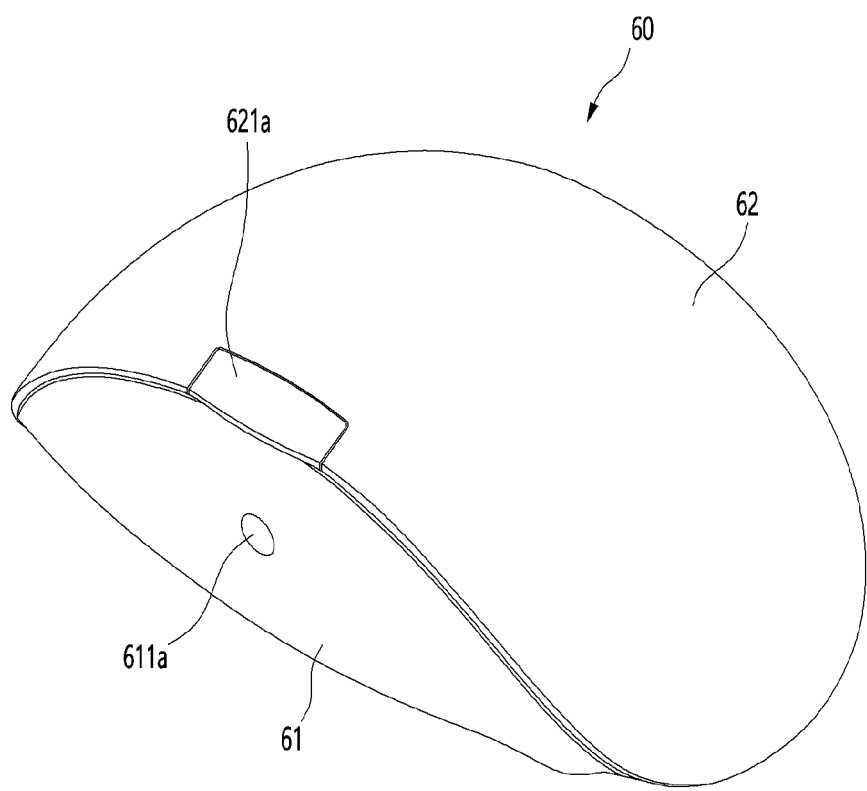
FIG. 1 is a front perspective view showing an example configuration of a sterilization case.
Figure 2:
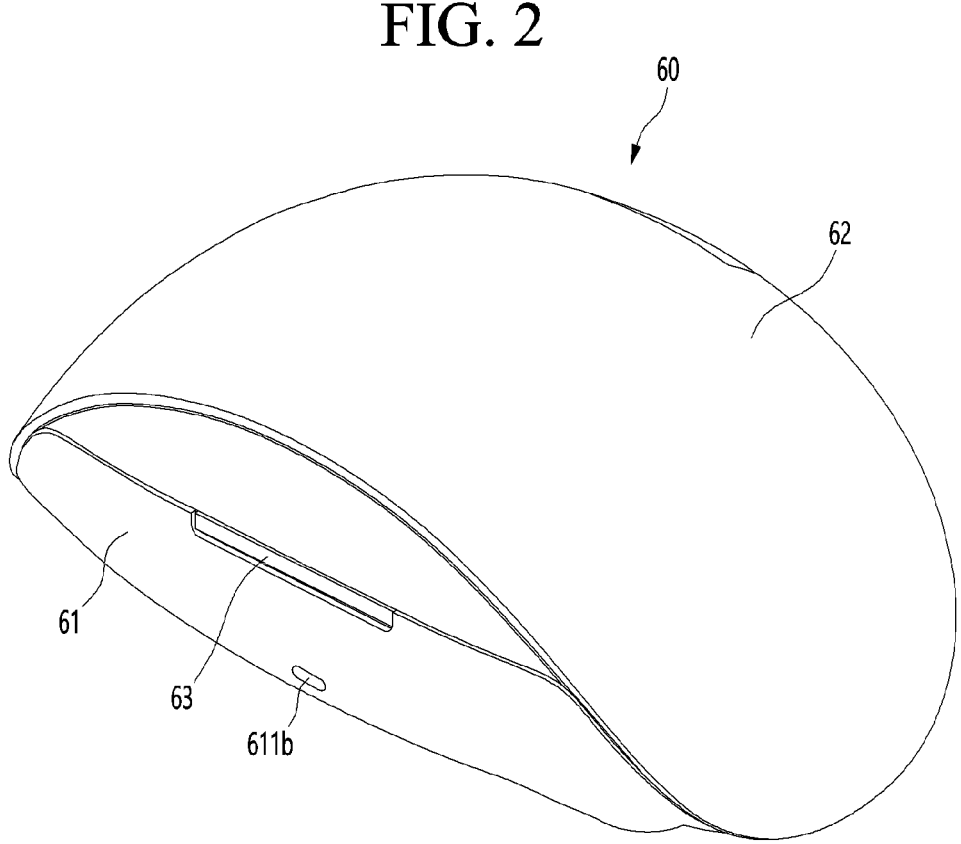
FIG. 2 is a rear perspective view showing an example configuration of a sterilization case.
Figure 3:
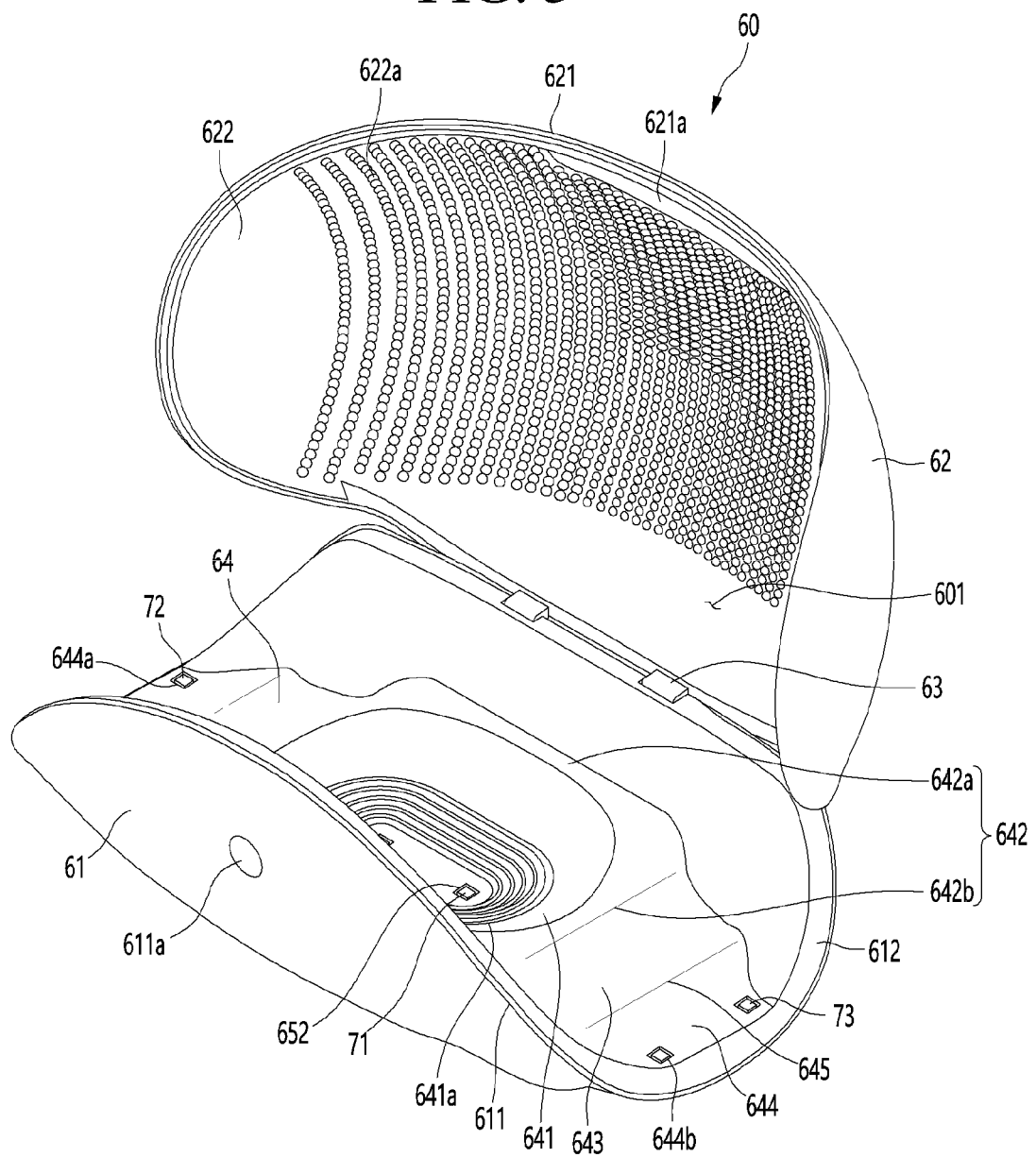
FIG. 3 is a front perspective view showing an example configuration of a sterilization case wherein the sterilization case is open.

FIG. 1 is a front perspective view of a sterilization case according to an implementation of the present disclosure, FIG. 2 is a rear perspective view of a sterilization case according to an implementation of the present disclosure, and FIG. 3 is a front perspective view in a state in which a sterilization case according to an implementation of the present disclosure is open.

Referring to FIGS. 1 to 3, a sterilization case 60 according to the present disclosure is configured to sterilize a mask device 1 stored therein.

Here, a mask device 1 may be understood as a device for covering a user's nose and mouth and preventing foreign substances in the air from entering the user's nose and mouth.

The sterilization case 60 may include a case body 61 supporting the mask device 1 and a case cover 62 rotatably coupled to the case body 61 to cover the mask device 1.

The case body 61 may be placed on a support surface to form a surface supporting the mask device 1, and the case cover 62 may be coupled to the case body 61 to form an accommodation space 601 inside the sterilization case 60.

The case body 61 may be formed in a shape in which front and rear sides thereof are blocked and an upper side and both sides on each end are open. In addition, when the case cover 62 is coupled to the case body 61, the inside of the case body 61 may be sealed by the upper side and both sides on each end of the case cover. That is, when the case body 61 and the case cover 62 are coupled, a shielded space is formed inside the sterilization case 60.

In some implementations, the case cover 62 is rotatably coupled to the upper portion of the case body 61. In some implementations, the case cover 62 is coupled to the edge of the upper end of the case body 61 through a hinge 63.

The case cover 62 may be provided to partially or entirely cover the opened upper surface of the case body 61. For example, the case cover 62 may be formed in a hollow dome shape.

The case cover 62 may be formed in a shape in which a lower end or lower edge thereof is engaged with an upper end or upper edge of the case body 61. Accordingly, when the case cover 62 rotates in an open direction, the accommodation space 601 may be exposed, and, when the case cover 62 rotates in a closed direction, the accommodation space 601 may be completely shielded.

For example, a groove may be formed along the edge of any one of the case body 61 and the case cover 62, and a rib may be formed along the edge of the other of the case body 61 and the case cover 62. In addition, when the case cover 62 and the case body 61 are coupled, the rib may be inserted into the groove.

In some implementations, the case cover 62 is provided with a cover coupling portion 621a. The cover coupling portion 621a may perform a function for stably coupling the case cover 62 to the case body 61.

The cover coupling portion 621a may be provided with a first magnet having a first polarity. In addition, the case body 61 corresponding to the cover coupling portion 621a may be provided with a second magnet having a second polarity. Here, any one of the first polarity and the second polarity may be an N-pole and the other thereof may be an S-pole.

That is, when the case cover 62 rotates in a closed direction, the first magnet of the cover coupling portion 621a and the second magnet of the case body 61 may be in close contact with each other by attraction. As a result, the case cover 62 may be more conveniently closed to provide a locking function. In addition, in some implementations, even if a user picks up the sterilization case 60 in an upside down state, the case cover 62 will not automatically open due to its own weight.

The cover coupling portion 621a may be provided on an edge portion of the case cover 62. A groove capable of being caught by a user's finger may be defined in the cover coupling portion 621a, such that the case cover 62 is opened in an open direction.

In some implementations, it is possible that a structure in which an elastic hook protrudes at a portion where the cover coupling portion 621a is formed and a locking groove or a locking protrusion for engaging the elastic hook is provided at the edge of the case body 61.

The case cover 62 may include an outer cover 621 establishing an outer appearance thereof and an inner cover 622 coupled to an inner side of the outer cover 621.

The outer cover 621 forms an outer surface of the case cover 62, and the inner cover 622 forms an inner surface of the case cover 62. The inner cover 622 can be designed to have a shape corresponding to that of the outer cover 621 and may be superposed on the inner side of the outer cover 621. That is, the thickness of the case cover 62 may be uniformly formed. However, the curvature of the inner cover 622 can be different from that of the outer cover 621, such that a space may be formed between the outer cover 621 and the inner cover 622, and the space may function as a heat insulating layer.

However, the case cover 62 is not limited to a structure composed of the inner cover 622 and the outer cover 621, and a structure composed of a single cover is not excluded. When the case cover 62 is composed of a single cover, the outer surface of the cover can perform the function of the outer cover 621, and the inner surface of the cover can perform the function of the inner cover 622.

The inner cover 622 may be provided with a reflective pattern 622a configured to reflect ultraviolet light. The reflective pattern 622a may reflect the ultraviolet light irradiated from sterilization modules 72 and 73 provided in the case body 61 such that the ultraviolet light is irradiated onto the surface of the mask device 1.

For example, the reflective pattern 622a may include a plurality of protrusions protruding from the surface of the inner cover 622. The protrusions may have a hemispherical or polygonal pyramid shape. For example, the reflective pattern 622a may comprise a hemispherical protrusion pattern or a hexagonal pyramidal pattern arranged on the surface of the inner cover 622 at predetermined intervals. In some cases, the reflective pattern 622a can be integrally formed with the inner cover 622. In some cases, the reflective pattern 622a can be formed separately from the inner cover 622 and subsequently attached.

In other examples, the reflective pattern 622a may include a plurality of linear ribs protruding from the surface of the inner cover 622. The linear ribs may have a hemispherical or triangular pyramid shape. Specifically, the plurality of linear ribs defining the reflective pattern 622a may extend in the width direction of the inner cover 622, and a plurality of the protrusions may be arranged in the length direction of the inner cover 622 at predetermined intervals. Here, the length of the inner cover 622 may be greater than the width thereof.

The case body 61 may include a power switch 611a for turning the sterilization case 60 on or off. The power switch 611a may be disposed on the front surface of the case body 61.

When the power switch 611a is turned on, the sterilization modules 71, 72 and 73 provided in the sterilization case 60 are configured to operate. However, even when the power switch 611a is turned on, control may be performed such that the sterilization modules 71, 72 and 73 operate only when the case cover 62 is closed and the sterilization modules 71, 72 and 73 do not operate when the case cover 62 is open.

The case body 61 may include a connector terminal 611b configured to connect the case body 61 to a cable or wire from the outside. The connector terminal 611b may be disposed on a rear surface of the case body 61.

For example, when a charging cable connected to an external power source is connected to the connector terminal 611b, a battery installed in the sterilization case 60 may be charged.

Hereinafter, directions are defined in detail. In FIG. 1, a direction in which the power switch 611a faces outward is defined as a "front direction" and a direction opposite to the front direction, that is, a direction in which the connector terminal 611b faces outward, is defined as a "rear direction".

Alternatively, a direction parallel to a direction from the connector terminal 611b towards the power switch 611a may be defined as a "front direction" and an opposite direction of the front direction thereof may be defined as a "rear direction".

In FIG. 1, the sterilization case 60 may have a shape with a width W, wherein the width W is predetermined in a front-and-rear direction, and a length L in a direction perpendicular to the width W and extending in both lateral directions. In addition, the length L of the sterilization case 60 may be designed to be greater than the width W.

Similarly to the case cover 62, the case body 61 may include an outer case 611 forming an outer appearance thereof and an inner case 612 coupled to the inner side of the outer case 611. The outer case 611 forms an outer surface of the case body 61, and the inner case 612 forms an inner surface of the case body 61.

The outer case 611 may define a case seating surface in contact with a surface on which the sterilization case 60 is placed, and the inner case 612 may define a seating surface 64 on which the mask device 1 is seated. The inner case 612 may have a shape corresponding to that of the outer case 611 and may be superposed on the inner side of the outer case 611. Therefore, an installation space in which electric parts are installed may be formed between the outer case 611 and the inner case 612.

The seating surface 64 is a part on which the mask device 1 may be seated, and may include a plurality of curved portions such that the mask device 1 is stably supported. The seating surface 64 may be disposed apart from the bottom surface of the outer case 611 at a predetermined height.

According to an implementation, the seating surface 64 may include a first recessed part 641 having a central portion recessed downward, a second recessed part 643 recessed downward from the edge of the first recessed part 641, a support part 642 formed between the first recessed part 641 and the second recessed part 643, a third recessed part 644 extending laterally from the second recessed part 643 and further recessed downward, and a boundary part 645 bordering the second recessed part 643 and the third recessed part 644.

The support part 642 may include a boundary part 642b bordering the first recessed part 641 and the second recessed part 643, and a support surface 642a defined as a region between the front and rear ends of the first recessed part 641 and an edge of the seating surface 64.

The boundary part 642b may be defined as a first boundary part, and the boundary part 645 may be defined as a second boundary part. Hereinafter, the first boundary part 642b and the second boundary part 645 will be described.

The first recessed part 641 is formed at the center of the seating surface 64, and the first boundary part 642b, the second recessed part 643, the second boundary part 645 and the third recessed part 644 may be sequentially arranged from both side ends of the first recessed part 641.

The seating surface 64 may be symmetrically formed with respect to a vertical axis extending in the front-and-rear direction of the sterilization case 60 and/or a vertical axis extending in the left-and-right direction of the sterilization case 60 while passing through the center of the seating surface 64. That is, the seating surface 64 may have a shape which is symmetrical in the left-and-right direction and/or the front-and-rear direction.

An opening 641a configured to accommodate a ventilation grill 65 can be formed in the first recessed part 641. The opening 641a may be formed by cutting a portion of the first recessed part 641. The opening 641a may be formed in a circular or elliptical shape.

The edge of the ventilation grill 65 may be fixed and supported on the inner edge of the opening 641a. The ventilation grill 65 may be formed such that the shape thereof corresponds to that of the opening 641a, and may include a grill part 651 configured to allow air to pass. In addition, a first exposure port 652 configured to expose the first sterilization module 71 may be formed in the bottom of the grill part 651.

The number of first exposure ports 652 formed in the bottom of the grill part 651 may correspond to the number of LED devices in the first sterilization module 71. For example, two first exposure ports 652 may be formed in correspondence with two LED devices and may be formed at positions corresponding to points where the two LED devices are disposed. More specifically, the two first exposure ports 652 may be formed at the left and right edges of the ventilation grill 65.

The support part 642 can serve to support the central portions of the mask device 1, with which a nasal bone and chin are respectively in contact. When the mask device 1 is seated on the seating surface 64, the central portions of the mask device 1 may be in contact with the support part 642 to be supported.

Specifically, the support part 642 may include a support surface 642a formed on front and rear sides of the first recessed part 641 and a first boundary part 642b formed at both side ends of the first recessed part 641.

In some implementations, the height of the support surface 642a is greater than that of the first boundary part 642b, such that, when the mask device 1 is seated on the seating surface 64, the mask device 1 is in contact with the support surface 642a and is spaced apart from the first boundary part 642b.

The mask device 1 may be spaced apart from the first boundary part 642b in order to allow irradiation of ultraviolet rays onto the bottom surface of the mask device 1 and to facilitate air circulation by the ventilation grill 65.

The second recessed part 643 may serve to support both ends of the mask device 1. When the mask device 1 is seated on the seating surface 64, both ends of the mask device 1 may be seated on the inner side of the second recessed part 643 to be supported.

A second exposure port 644a configured to expose the second sterilization module 72 may be formed in the third recessed part 644 located on the left and a third exposure port 644b configured to expose the third sterilization module 73 may be formed in the third recessed part 644 located on the right.

In some implementations, the third recessed part 644 is configured to define a space between the seating surface 64 of the case body 61 and the inner cover 622 of the case cover 62, allowing ultraviolet light irradiated from the second and third sterilization modules 72 and 73 to be sufficiently transmitted to the reflective pattern 622a.

Figure 4:
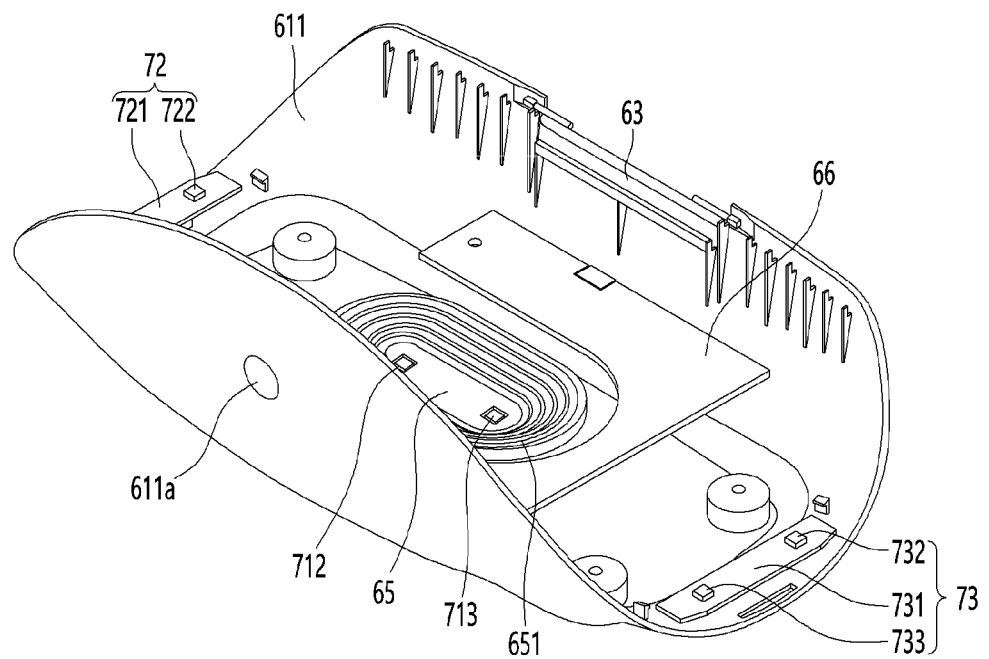
FIG. 4 is a front perspective view showing an example configuration of a sterilization case body wherein an inner case is removed.
Figure 5:
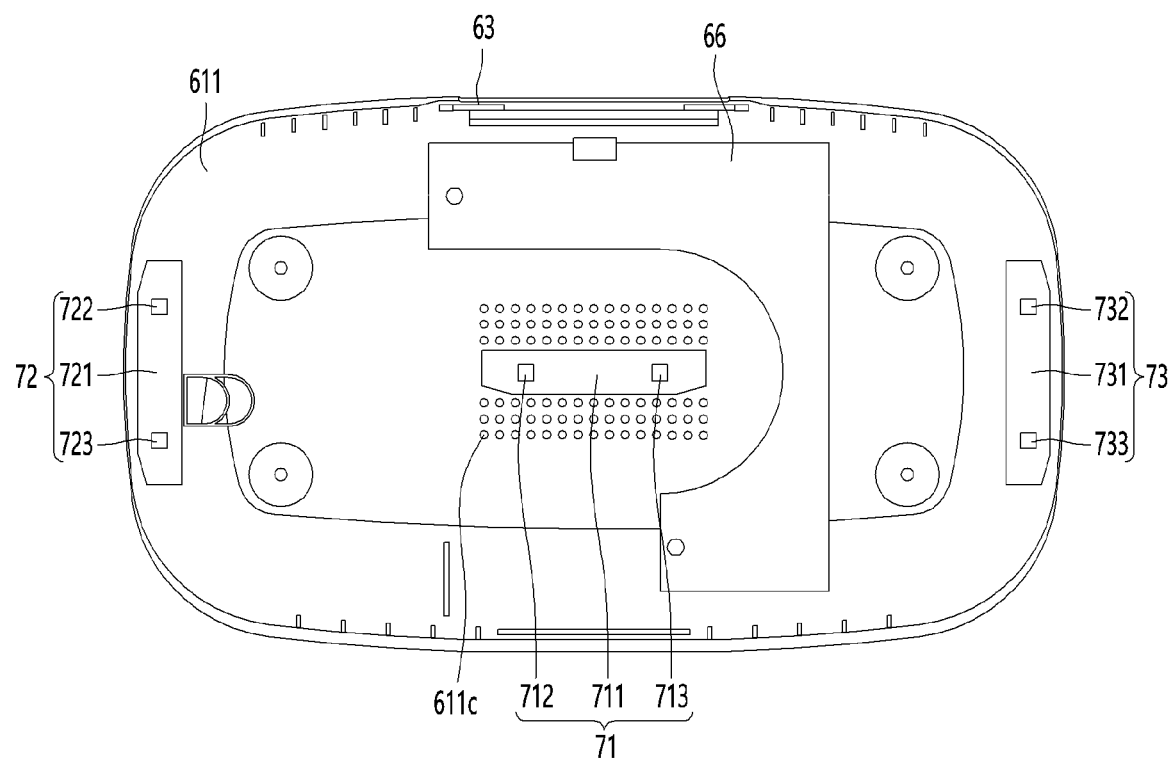
FIG. 5 is a plan view showing an example configuration of an outer case with ventilation holes formed in the outer case of FIG. 4.

FIG. 4 is a front perspective view showing the configuration of a case body according to an implementation of the present disclosure in a state in which an inner case is removed, and FIG. 5 is a plan view of an outer case showing a ventilation hole formed in the outer case of FIG. 4.

Referring to FIGS. 4 and 5, the sterilization case 60 may include the sterilization modules 71, 72 and 73 configured to sterilize the mask device 1.

The sterilization modules 71, 72 and 73 may be disposed inside the case body 61 to irradiate ultraviolet rays onto the surface of the mask device 1 placed on the case body 61. The sterilization modules 71, 72 and 73 may be disposed in an inner installation space (see 602 of FIG. 9) defined by combining the outer case 611 and the inner case 612.

The sterilization modules 71, 72 and 73 may include one or a plurality of first sterilization modules 71 located at the center of the case body 61, and the second and third sterilization modules 72 and 73 located at both edges of the case body 61.

Specifically, each of the sterilization modules 71, 72 and 73 may include a board 711, 721 and 731 and one or a plurality of LED devices 712, 713, 722, 723, 732 and 733 disposed on the board 711, 721 and 731.

For example, the board 711, 721 and 731 may have a flat bar shape, and two LED devices may be mounted on the board 711, 721, and 731 spaced apart from each other. An LED device may emit ultraviolet light having a wavelength of 10 to 40 nanometers.

The first sterilization module 71 is disposed on the center of the case body 61 to sterilize the bottom surface of the mask device 1, and serves to intensively sterilize the center of the mask device 1 covering the user's mouth and nose.

The first sterilization module 71 may be disposed under the ventilation grill 65. In addition, the first and second LED devices 712 and 713 of the first sterilization module 71 may be exposed to the outside through the first exposure port 652 formed in the bottom of the ventilation grill 65. Therefore, ultraviolet light generated by the first sterilization module 71 may be directed upward to intensively sterilize the center of the bottom surface of the mask device 1.

The second sterilization module 72 and the third sterilization module 73 are disposed on the left and right edges of the case body 61 to sterilize the upper surface of the mask device 1. The second sterilization module 72 and the third sterilization module 73 may be disposed under the third recessed part 644 of the seating surface 64.

In addition, the first and second LED devices 722 and 723 of the second sterilization module 72 and the first and second LED devices 732 and 733 of the third sterilization module 73 may be exposed to the outside through the second exposure port 644a and the third exposure port 644b formed in the third recessed part 644. As a result, ultraviolet light generated by the second sterilization module 72 and the third sterilization module 73 may be directed upward to be irradiated onto the inner surface of the case cover 62. In addition, light irradiated onto the inner surface of the case cover 62 may be specularly reflected and irradiated onto the upper surface of the mask device 1.

The sterilization case 60 may include a ventilation grill 65 coupled to the inner case 612. The ventilation grill 65 may have an elliptical shape and includes a grill part 651, configured to allow air to pass through. The grill part 651 may extend from the bottom edge of the ventilation grill 65 in a radial direction or radially.

Specifically, the ventilation grill 65 may include a flat bottom portion and a side portion extending to be upwardly inclined from the edge of the flat bottom portion, and the grill part 651 may be formed in the side portion.

The side portion of the ventilation grill 65 may have a smooth inclined surface or a stepped inclined surface. Specifically, when the side portion of the ventilation grill 65 is formed in a stepped shape, holes or slits defining the grill part 651 may be formed in a flat surface to define a step. This allows air flowing from the outside to the inside of the sterilization case 60 to flow upward without flow resistance.

The ventilation grill 65 may be coupled by a coupling rib provided on the inner side of the inner case 612. The ventilation grill 65 may be provided into the opening 641a of the inner case 612 to shield the opening 641a.

In some implementations, the first sterilization module 71 is coupled to the bottom surface of the ventilation grill 65. In addition, the first exposure port 652 configured to expose the first and second LED devices 712 and 713 of the first sterilization module 71 is formed in the bottom of the ventilation grill 65.

The sterilization case 60 may include a main control board 66 configured to control the sterilization modules 71, 72 and 73 and the electric parts installed in the sterilization case 60.

The main control board 66 is placed in a space formed between the outer case 611 and the inner case 612. The main control board 66 may be formed in an L-shape or U-shape. The main control board 66 may be located on the lower center of the inner case 612 and may be disposed to surround the edge of the ventilation grill 65.

The main control board 66 may be provided with a power source and a battery for supplying power to the sterilization modules 71, 72 and 73.

The main control board 66 may be coupled and fixed to the lower portion of the inner case 612 or may be coupled and fixed to a rib extending from the inner side of the outer case 611.

A ventilation hole 611c, configured to allow air to pass through, may be formed in the case body 61. The ventilation hole 611c may be formed in the bottom surface of the outer case 611.

For example, the ventilation hole 611c may be formed in the center of the bottom surface of the outer case 611. That is, the ventilation hole 611c may be disposed directly under the ventilation grill 65. Therefore, when air is sucked into the ventilation hole 611c, the air may be sterilized by the first sterilization module 71 and circulated in the case body 61 after passing through the grill part 651 of the ventilation grill 65.

In some implementations, the flow of air sucked through the ventilation hole 611c, the sterilization modules 71, 72 and 73 and the main control board 66 may be cooled in an air cooling manner.

Figure 6:
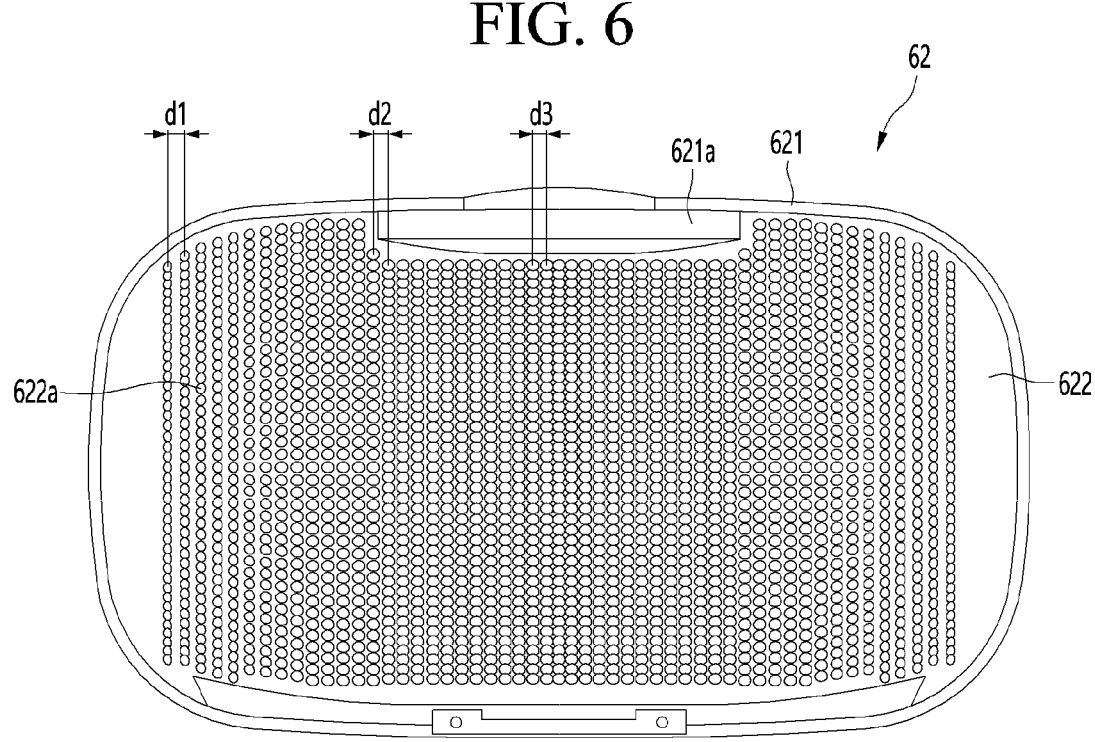
FIG. 6 is a bottom view showing an example configuration of a case cover of a sterilization case.
Figure 7:
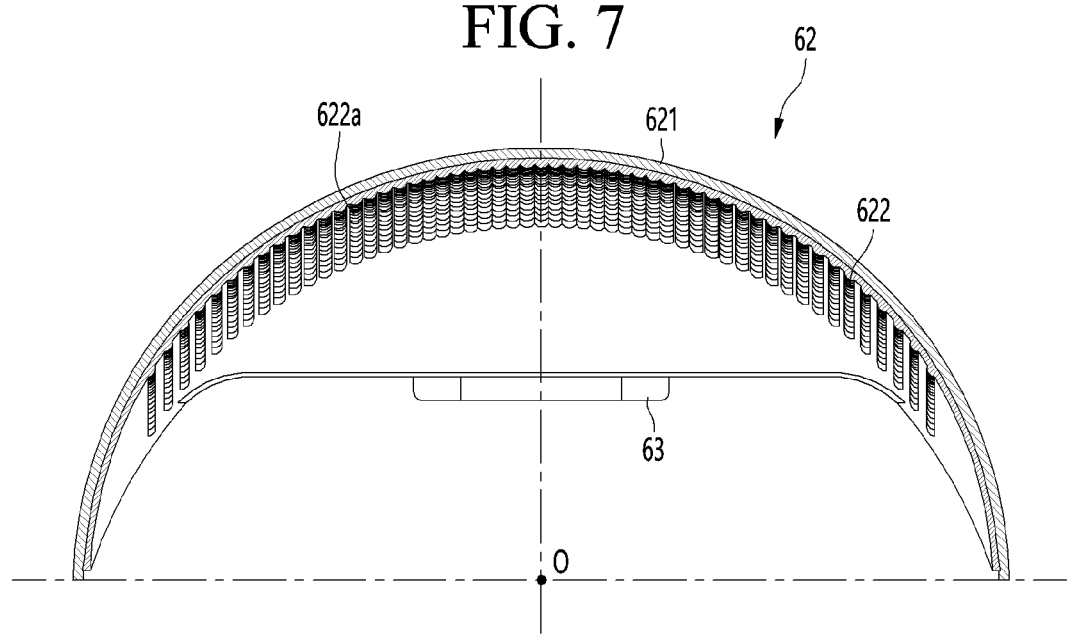
FIG. 7 is a cross-sectional view showing an example configuration of the cross-sectional shape of the case cover of FIG. 6.

FIG. 6 is a bottom view of a case cover according to an implementation of the present disclosure, and FIG. 7 is a cross-sectional view showing the cross-sectional shape of a case cover according to an implementation of the present disclosure.

Referring to FIGS. 6 and 7, as described above, the case cover 62 according to the present disclosure includes the outer cover 621 forming an outer appearance and the inner cover 622 coupled to the inner surface of the outer cover 621.

The outer cover 621 can be formed to have a semicircular or hemispherical shape, and the inner cover 622 can be formed in a shape corresponding to that of the outer cover 621 and is coupled to the inner surface of the outer cover 621.

The cover coupling portion 621a for stably coupling the case cover 62 to the case body 61 is provided at one edge of the inner cover 622.

The cover coupling portion 621a may be provided with a first magnet having a first polarity. In addition, a position on the case body 61 corresponding to the cover coupling portion 621a may be provided with a second magnet having a second polarity. Here, any one of the first polarity and the second polarity may be an N-pole and the other thereof may be an S-pole.

That is, when the case cover 62 rotates in a closed direction, the first magnet of the cover coupling portion 621a becomes close to the second magnet of the case body 61, such that they are magnetically coupled due to attraction. Therefore, the case cover 62 may be easily closed to provide a locking function.

A hinge 63 rotatably connected to the case body 61 is provided on the other edge of the inner cover 622 corresponding to the opposite side of the cover coupling portion 621a.

The inner cover 622 may be provided with a reflective pattern 622a configured to reflect ultraviolet light. The reflective pattern 622a serves to reflect and irradiate ultraviolet light irradiated by the sterilization modules 71, 72 and 73 to the upper surface of the mask device 1.

The reflective pattern 622a may have a smooth surface with nano-scale roughness for specular reflection. The reflective pattern 622a may have a specific or random pattern at macro-scale or micro-scale.

For example, the reflective pattern 622a may include a plurality of protrusions protruding from the surface of the inner cover 622. The reflective pattern 622a may be a lattice pattern or an embossed pattern. Each of the plurality of protrusions may have a circular or polygonal transverse cross section. In the present implementation, the reflective pattern 622a has a hemispherical configuration or structure, wherein the plurality of protrusions have a circular transverse section and are spaced apart from each other in a lattice shape.

The reflective pattern 622a may be applied to the entire surface of the inner cover 622. In this case, the reflective pattern 622a may have a structure wherein a density of the plurality of protrusions defining the reflective pattern increases from the edge towards the center of the inner cover 622.

That is, the reflective pattern 622a may have a structure that a column gap between adjacent protrusions may become narrower from the edge towards the center of the inner cover 622. In this case, the column gap d3 between the protrusions located at the center of the inner cover 622 is narrower than the column gap d1 between the protrusions located at the edge of the inner cover 622.

When the column gap between the protrusions located at the center of the inner cover 622 becomes narrower, ultraviolet rays emitted from the sterilization modules 71, 72 and 73 may be irradiated onto the protrusions corresponding to the center of the inner cover 622 and the ultraviolet rays specularly reflected by the protrusions may be intensively irradiated onto the upper surface of the mask device 1.

By adjusting the irradiation angle of the reflective pattern 622a according to the specular reflection principle of the reflective pattern 622a, it is possible to adjust the intensity of illumination and sterilization efficiency of the upper surface of the mask device 1 at a desired location. That is, since ultraviolet light may be uniformly irradiated onto the upper portion or upper surface of the mask device 1, sterilization of which is relatively difficult, it is possible to shorten sterilization time and minimize deterioration due to exposure to ultraviolet rays.

In addition, in order to increase reflectivity of the ultraviolet rays, the inner cover 622 and/or the reflective pattern 622a may be coated or plated. For example, the reflective pattern 622a may be coated with a metal material such as chrome (Cr), gold (Au), silver (Ag), copper (Cu), zinc (Zn), or the like, thereby improving reflectivity.

In some implementations, wherein the reflective pattern 622a is configured in a hemispherical pattern, the reflection angle may be designed by adjusting a diameter, a height and a pitch (column gap) of the protrusions according to the shape of the case cover 62.

In the present implementation, the diameter of a hemispherical protrusion may be 3.5 mm and the height of the protrusion may be 0.5 mm.

Figure 8:
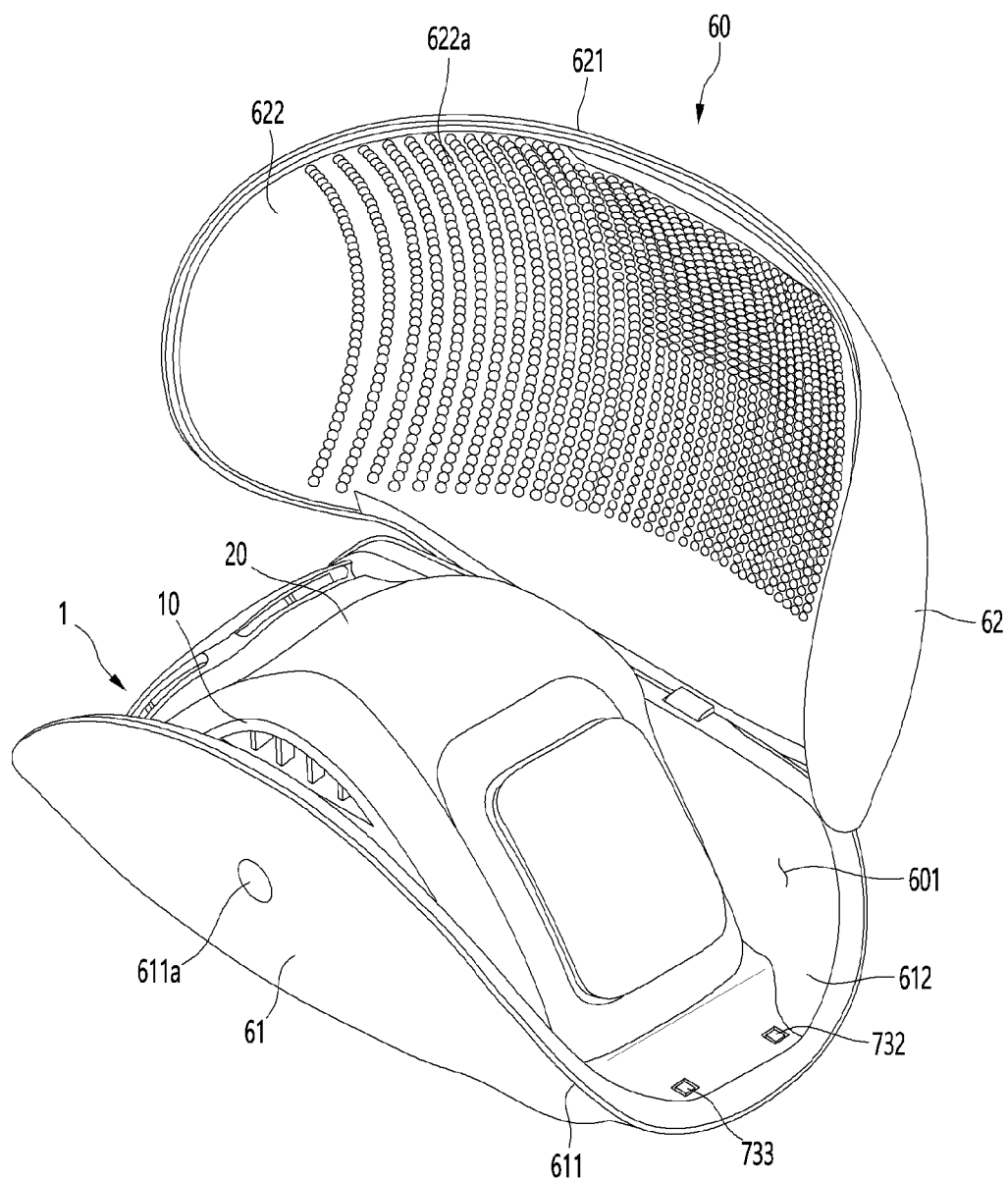
FIG. 8 is a view showing an example configuration of a sterilization case, wherein a mask device is stored in the sterilization case.
Figure 9:
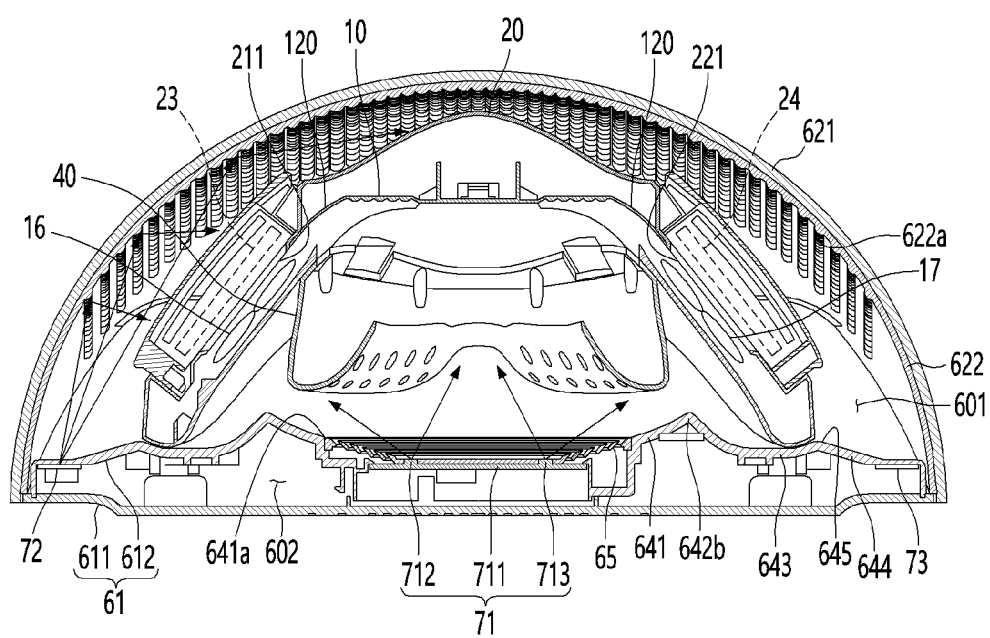
FIGS. 9 and 10 are cross-sectional views showing an example configuration of the vertical cross-section of the sterilization case of FIG. 8.
Figure 10:
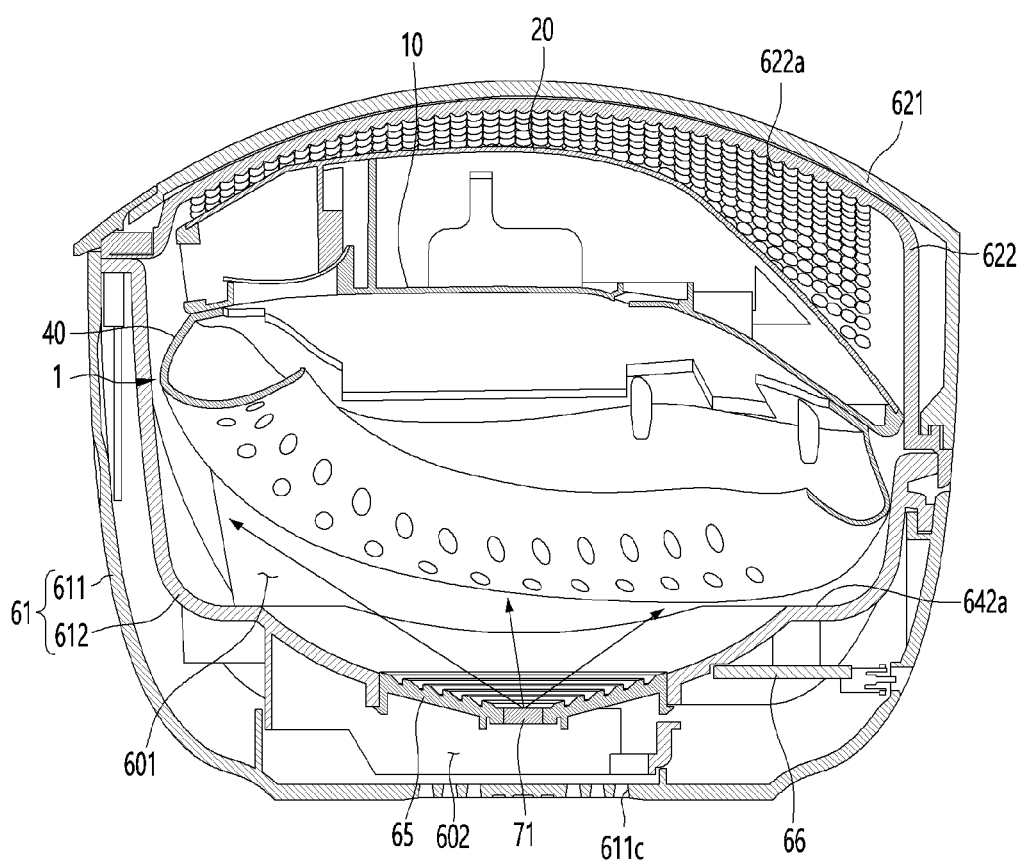

FIG. 8 is a view of a sterilization case showing a state in which a mask device is stored in the sterilization case according to an implementation of the present disclosure, and FIGS. 9 and 10 are cross-sectional views showing the vertical cross-section of the sterilization case of FIG. 8.

Referring to FIGS. 8 to 10, as described above, the mask device 1 may be stored in the sterilization case 60. The mask device 1 may be seated on the seating surface 64 formed in the case body 61, and, when the case cover 62 is rotated and closed, the mask device 1 can thus be sealed and protected.

Specifically, when the mask device 1 is seated on the seating surface 64, at least a portion of the center of the mask device 1 may be supported on the support surface 642a of the seating surface 64 and both ends of the mask device 1 may be supported on the second recessed part 643 of the seating surface 64.

At this time, the support surface 642a supports the inner side of the sealing part 40 of the mask device 1, and the second recessed part 643 has a recessed shape such that both ends of the mask device 1 are seated. Accordingly, the mask device 1 may be easily mounted in the sterilization case 60, and may be stably stored within the sterilization case 60. Thus, for instance, the mask device 1 can be stored within the sterilization case 60 without being shaken and potentially damaged as a result. Here, in a state in which the mask device 1 is seated on the seating surface 64, the sealing part 40 may be spaced apart from the seating surface 64.

The mask device 1 may include a mask body 10 covering a person's face and a sealing part 40 which is coupled to the center of the mask body 10 and is in close contact with the person's face to form a breathing space therein.

The mask device 1 may further include a mask body cover 20 coupled to the mask body 10. The mask body cover 20 may be coupled to the front surface (or the upper surface) of the mask body 10, and the sealing part 40 may be coupled to the rear surface (or the lower surface) of the mask body 10.

Referring to FIG. 9, the mask body cover 20 may be disposed on the upper surface of the mask body 10, and the sealing part 40 may be disposed on the lower surface of the mask body 10.

The mask body 10 may be elongated in the left-and-right direction and the center portion thereof may be convexly rounded upward. The left and right of the mask body 10 may be symmetrically formed.

The sealing part 40 may be formed in a closed loop shape to define the breathing space therein. The sealing part 40 may be detachably coupled to the lower surface of the mask body 10.

When the mask device 1 is seated on the seating surface 64, the sealing part 40 may be in contact with and supported on the support surface 642a. In addition, both ends of the mask body 10 may be in contact with and supported on the second recessed part 643.

By separating the sealing part 40 of the mask device 1 from the first boundary part 642b, it is possible to irradiate ultraviolet rays to the lower portion of the seating surface 64 on which the mask device 1 is seated and to facilitate air circulation by the ventilation grill 65.

In a state in which at least a portion of the sealing part 40 is supported on the support surface 642a of the support part 642, the inside of the sealing part 40 defining the breathing space, may face the first recessed part 641 or the ventilation grill 65.

As described above, when the mask device 1 is seated on the seating surface 64, the plurality of sterilization modules 71, 72 and 73 may be operated. At this time, the plurality of sterilization modules 71, 72 and 73 may all be disposed at the same height.

First, when the first sterilization module 71 disposed on the ventilation grill 65 is operated, ultraviolet light generated by the first sterilization module 71 is directed upward to be irradiated onto the bottom surface of the mask device 1. In this case, the rear surface of the mask body 10 and the surface of the sealing part 40 configured to be in close contact with the user's face may be sterilized by ultraviolet rays.

In particular, since a separation space is formed between the lower portion of the sealing part 40 and the first boundary part 642b, a portion of the ultraviolet light generated by the first sterilization module 71 may be irradiated not only onto the entire sealing part 40 but also onto the rear surface of the mask body 10 through the separation space.

When the second sterilization module 72 and the third sterilization module 73 are operated, some of the ultraviolet lights generated from the second sterilization module 72 and the third sterilization module 73 may spread into the space between the outer surface of the mask device 1 and the inner surface of the case cover 62.

In some implementations, ultraviolet light irradiated onto the inner cover 622 is specularly reflected by the reflective pattern 622a and is irradiated onto the outer surface of the mask device 1. In particular, the protrusions establishing the reflective pattern 622a are more densely disposed from the edge towards the center of the inner cover 622, allowing the ultraviolet light to uniformly irradiate onto the center portion of the mask device 1. In other words, although the amount of ultraviolet light irradiated onto the center of the inner cover 622 may be small, the ultraviolet rays are intensively irradiated onto the central portion of the outer surface of the mask device 1, since the density of the reflective pattern 622a is higher at the center of the inner cover 622. Accordingly, ultraviolet rays may be uniformly irradiated over the entire outer surface of the mask device 1.

In some examples, since ultraviolet light may be sufficiently irradiated onto the central portion of the outer surface of the mask device 1, sterilization of which is relatively difficult, it is possible to shorten sterilization time and minimize deterioration of the outer surface of the mask device 1 due to exposure to ultraviolet rays.

In another implementation of the present disclosure, the second sterilization module 72 and the third sterilization module 73 may be disposed at a higher installation height than the first sterilization module 71. In some implementations, the installation heights of the second sterilization module 72 and the third sterilization module 73 may be the same.

According to such a configuration, since the installation height of the second sterilization module 72 and the third sterilization module 73 for irradiating ultraviolet light onto the side surface of the object to be sterilized and the inner surface of the case cover 62 is relatively higher than that of the first sterilization module 71, it is possible to irradiate ultraviolet rays more efficiently onto the upper portion or upper surface of the object to be sterilized.

Figure 11:
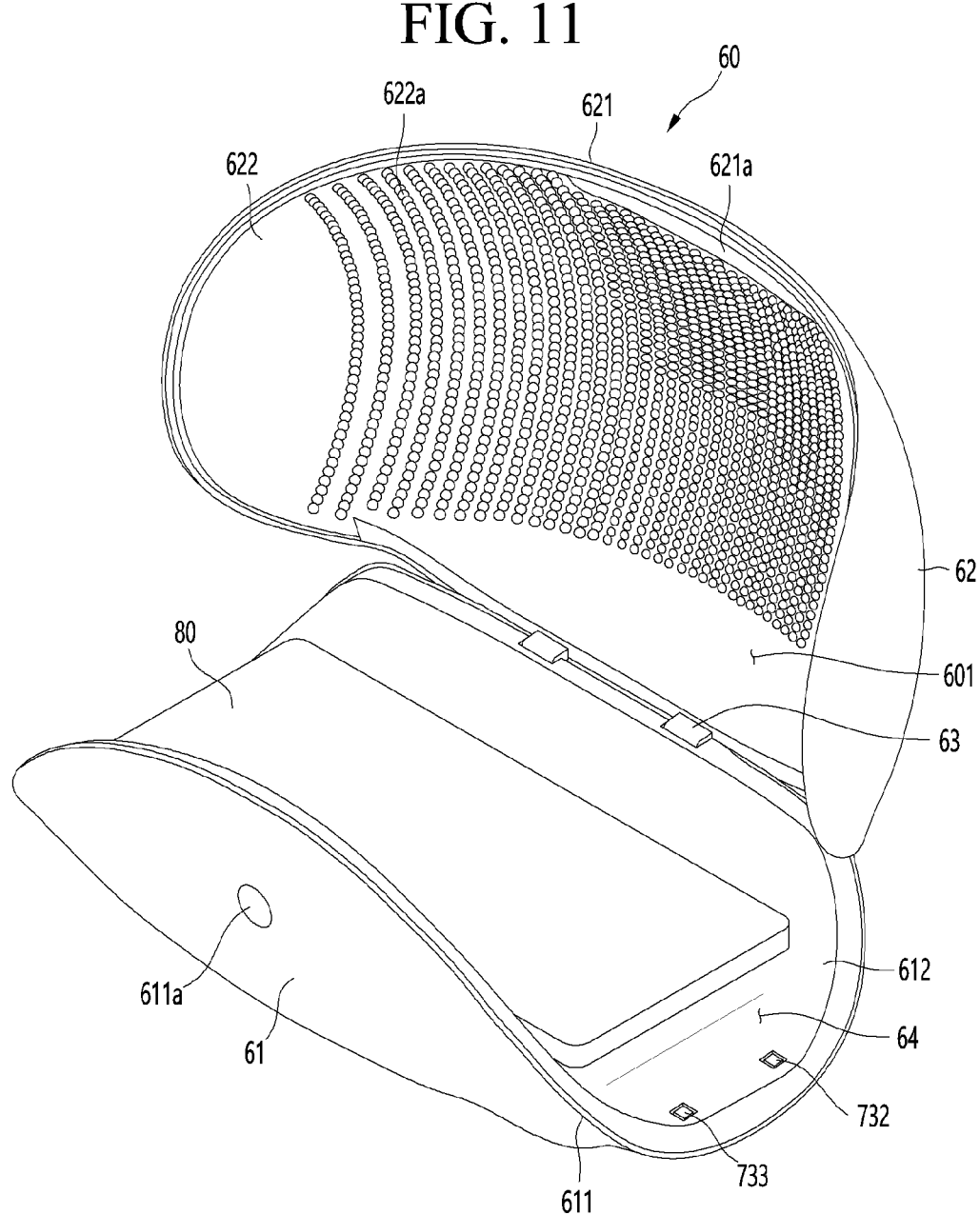
FIG. 11 is a view showing an example configuration of a sterilization case, wherein a portable terminal is stored in the sterilization case.
Figure 12:
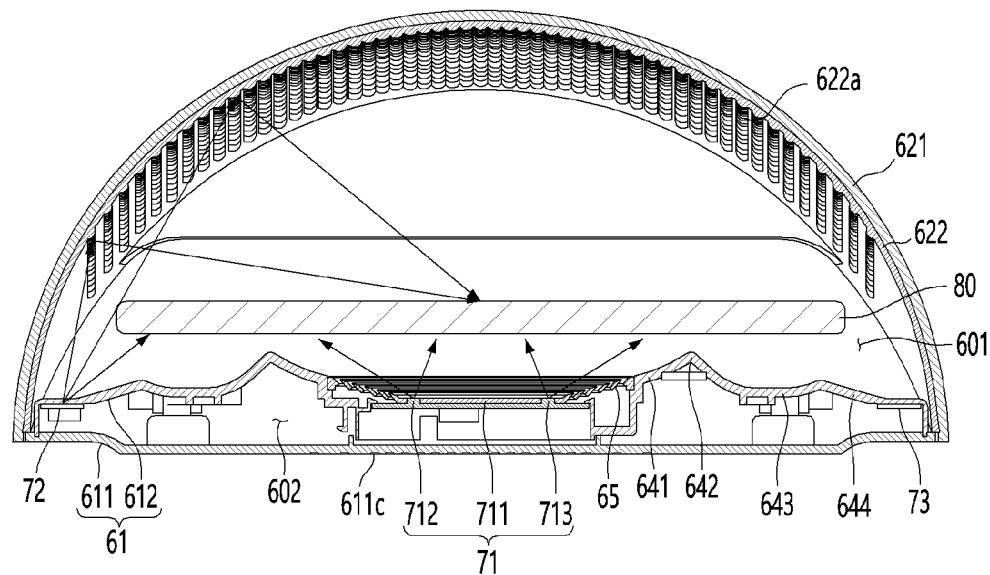
FIG. 12 is a cross-sectional view showing an example configuration of the vertical cross section of the sterilization case of FIG. 11.

FIG. 11 is a view showing a state in which a portable terminal is stored in a sterilization case according to an implementation of the present disclosure, and FIG. 12 is a cross-sectional view showing the vertical cross section of the sterilization case of FIG. 11.

Referring to FIGS. 11 and 12, a portable terminal 80 may be accommodated and sterilized in the sterilization case 60 according to the present disclosure. The portable terminal 80 may have a rectangular plate shape and may be placed in the sterilization case 60 having a length direction in the left-and-right direction of the sterilization case 60. The portable terminal 80 may be seated on the seating surface 64 formed in the case body 61, and, when the case cover 62 is rotated and closed, the portable terminal 80 may be sealed and protected.

When the portable terminal 80 is seated on the seating surface 64, the central portion of the portable terminal 80 may be supported on the support surface 642a of the seating surface 64.

In a state where the portable terminal 80 is supported on the support surface 642a, the lower surface of the portable terminal 80 may face the first recessed part 641 or the ventilation grill 65.

As described above, in a state in which the portable terminal 80 is seated on the seating surface 64, the plurality of sterilization modules 71, 72 and 73 may be operated. In some implementations, the plurality of sterilization modules 71, 72 and 73 may all be provided at the same height.

First, when the first sterilization module 71 disposed on the ventilation grill 65 is operated, ultraviolet light generated by the first sterilization module 71 may be irradiated onto the lower surface of the portable terminal 80, thereby sterilizing the lower surface of the portable terminal 80.

When the second sterilization module 72 and the third sterilization module 73 are operated, a portion of the ultraviolet rays generated by the second sterilization module 72 and the third sterilization module 73 may be irradiated onto the side surface of the portable terminal 80 and the remaining light may be irradiated onto the inner surface of the case cover 62.

The ultraviolet light irradiated onto the inner surface of the case cover 62 may be specularly reflected by the reflective pattern 622a and therefore irradiated onto the upper surface of the portable terminal 80.

As described above, the ultraviolet light emitted from the second and third sterilization modules 72 and 73 may be irradiated mostly onto the edge of the inner cover 622 and may be irradiated the least onto the center of the inner cover 622. In some implementations, the reflective pattern 622a is established by protrusions more densely disposed from the edge to the center of the inner cover 622, allowing the ultraviolet rays reflected by the reflective pattern 622a to be uniformly irradiated over the entire upper portion (upper surface) of the portable terminal 80.

According to such a configuration, not only a mask device but also the portable terminal may be stored and sterilized in the sterilization case. In addition, since ultraviolet rays may be uniformly irradiated not only onto the lower portion but also the upper portion of the portable terminal, it is possible to shorten sterilization time and minimize deterioration of the surface of the portable terminal due to exposure to ultraviolet rays.

Figure 13:
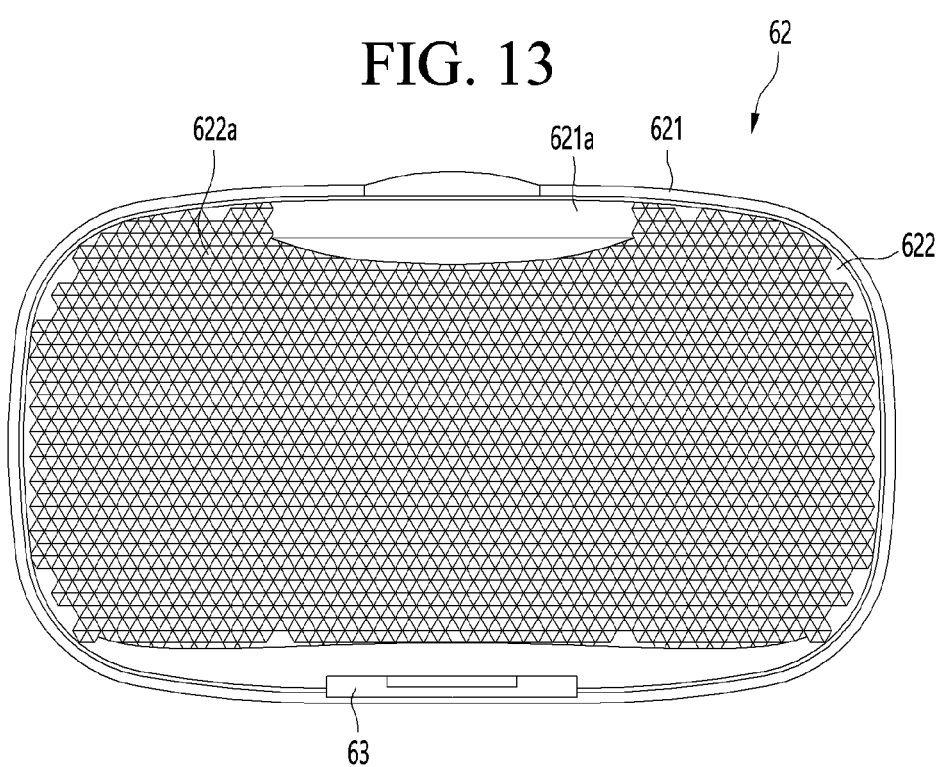
FIG. 13 is a bottom view showing an example configuration of a case cover.
Figure 14:
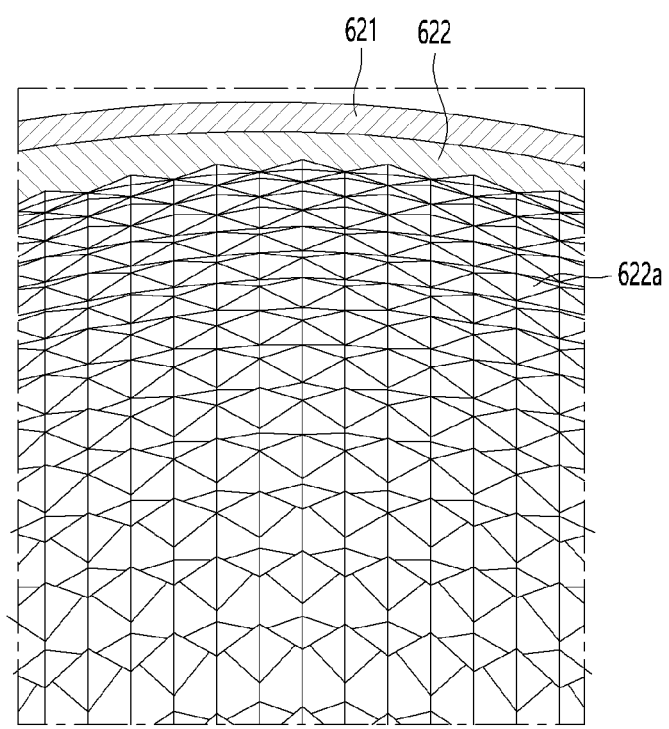
FIG. 14 is a cross-sectional view showing an example configuration the cross-sectional shape of a case cover.

FIG. 13 is a bottom view of a case cover according to another implementation of the present disclosure, and FIG. 14 is a cross-sectional view showing the cross-sectional shape of a case cover according to another implementation of the present disclosure.

The present implementation is the same as the above-described implementations in the other portions but different in the reflective pattern of the case cover. Accordingly, hereinafter, the characteristic portions of the present implementation will be described. For the same portions as the above-described implementations, refer to the above description.

Referring to FIGS. 13 and 14, in the present implementation, the reflective pattern 622a may be a hexagonal pyramid pattern.

The reflective pattern 622a may be applied to the entire surface of the inner cover 622. Specifically, in the hexagonal pyramid pattern, the side surfaces of the protrusion may be formed in six triangles and connected.

Accordingly, when ultraviolet light directed to the inner cover 622 is irradiated onto the side surfaces of the hexagonal pyramid pattern, the irradiated ultraviolet light may be specularly reflected and irradiated onto the upper portion of the mask device 1.

In the hexagonal pyramid pattern, it is possible to adjust the intensity of illumination and sterilization efficiency of the surface at a desired location by adjusting the diameter, height and pitch (gap) of each protrusion.

Figure 15:
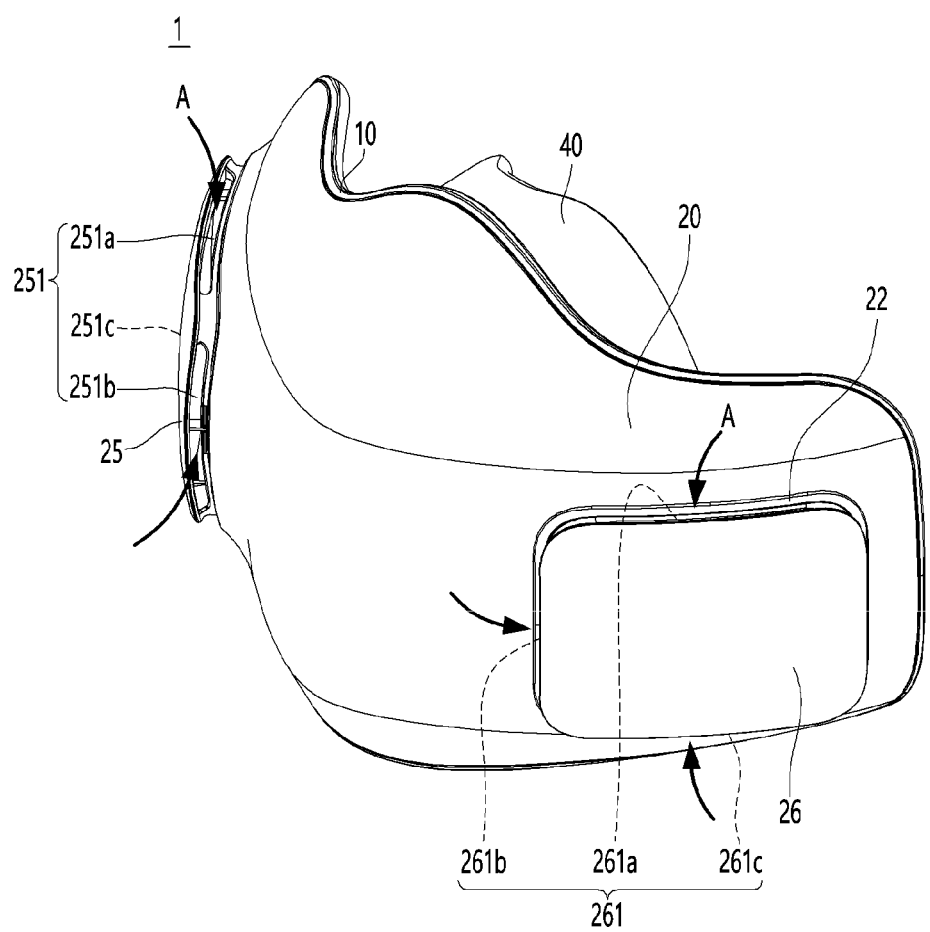
FIG. 15 is a left perspective view showing an example configuration of a mask device.
Figure 16:
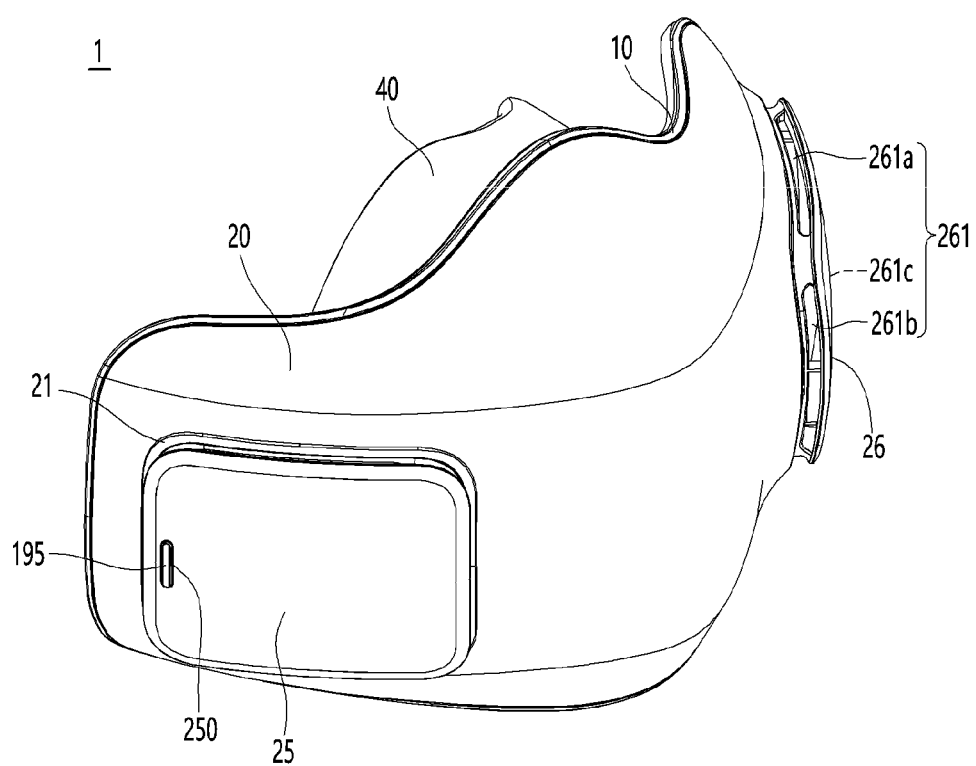
FIG. 16 is a right perspective view showing an example configuration of a mask device.
Figure 17:
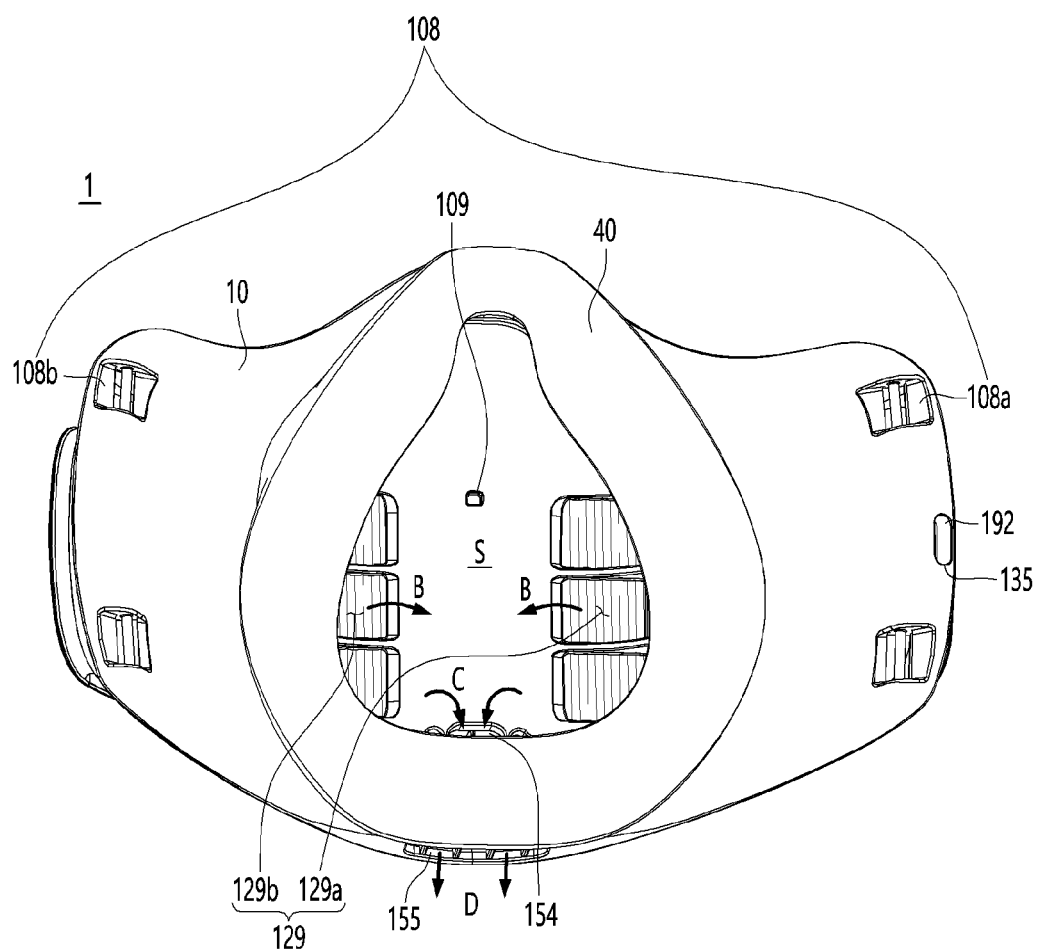
FIG. 17 is a rear view showing an example configuration of a mask device.
Figure 18:
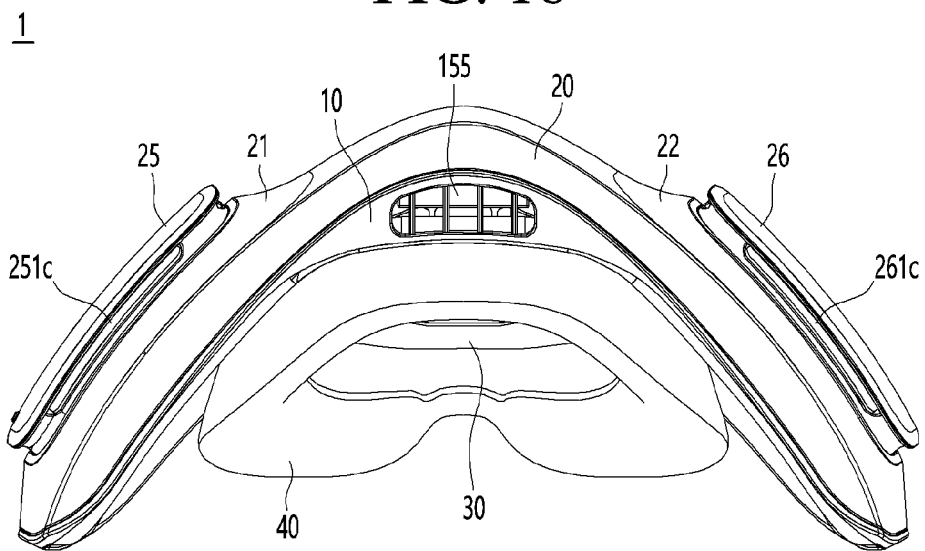
FIG. 18 is a bottom perspective view showing an example configuration of a mask device.

FIG. 15 is a left perspective view of a mask device according to an implementation of the present disclosure, FIG. 16 is a right perspective view of a mask device according to an implementation of the present disclosure, FIG. 17 is a rear view of a mask device according to an implementation of the present disclosure, and FIG. 18 is a bottom perspective view of a mask device according to an implementation of the present disclosure.

Referring to FIGS. 15 to 18, the mask device 1 according to the implementation of the present disclosure may include a mask body 10 and a mask body cover 20 coupled to the mask body 10.

The mask body 10 and the mask body cover 20 may be detachably coupled. When the mask body 10 and the mask body cover 20 are coupled, an inner space may be formed between the mask body 10 and the mask body cover 20. Components for operating the mask device 1 may be disposed in the inner space. The inner space may be formed between the front surface of the mask body 10 and the rear surface of the mask body cover 20. The mask body 10 may define the rear surface of the mask device 1, and the mask body cover 20 may define the front surface of the mask device 1.

The rear side of the mask device 1 defines a direction in which the rear surface of the mask device 1 facing a user's face is located and the front side of the mask device 1 is opposite to the rear side and defines a direction in which the front surface of the mask device 1 exposed to the outside is located.

The mask device 1 may further include a sealing bracket 30 and a sealing part 40 detachably coupled to the sealing bracket 30.

The sealing bracket 30 may be detachably coupled to the rear surface of the mask body 10, and the sealing part 40 may be fixed to the rear surface of the mask body 10. In addition, when the sealing bracket 30 is separated from the rear surface of the mask body 10, the sealing part 40 may be separated from the mask body 10.

The sealing part 40 is supported on the rear surface of the mask body 10 by the sealing bracket 30, and a breathing space S configured to allow for breathing may be defined between the sealing part 40 and the rear surface of the mask body 10. The sealing part 40 is in close contact with the user's face and wraps around the nose and mouth of the user to restrict external air from flowing into the breathing space S.

The mask body cover 20 may include a first filter mounting part 21 and a second filter mounting part 22. The first filter mounting part 21 may be located on the right side of the mask body cover 20, and the second filter mounting part 22 may be located on the left side of the mask body cover 20.

Based on the mask device 1 worn on the user's face, a left direction (a left side) and a right direction (a right side) are defined. That is, in a state in which a user wears the mask device 1, the right side of the user is defined as the right side of the mask device 1 and the left side of the user is defined as the left side of the mask device 1.

In addition, based on the mask device 1 worn on the user's face, an upward direction (upward) and a downward direction (downward) are defined.

A first filter cover 25 may be mounted in the first filter mounting part 21 and a second filter cover 26 may be mounted in the second filter mounting part 22. Filters may be disposed inside the first filter mounting part 21 and the second filter mounting part 22, and the first filter cover 25 and the second filter cover 26 may cover the filters.

The first filter cover 25 and the second filter cover 26 may be detachably coupled to the first filter mounting part 21 and the second filter mounting part 22, respectively. For example, the first filter cover 25 and the second filter cover 26 may be fitted into the first filter mounting part 21 and the second filter mounting part 22, respectively.

Each of the first filter cover 25 and the second filter cover 26 may include a front surface portion and a side surface portion extending rearward along the edge of the front surface portion or the edge of the rear surface.

Each of the side surface portions of the first filter cover 25 and the second filter cover 26 may include four side surfaces and the four side surfaces may include an upper side surface, a lower side surface, a left side surface and a right side surface.

One or a plurality of first air inlets 251 may be formed in the side surface portion of the first filter cover 25. One or a plurality of second air inlets 261 may be formed in the side surface portion of the second filter cover 26.

In a state in which the first filter cover 25 is mounted on the first filter mounting part 21, the first air inlet 251 may be formed to be exposed to the outside. In a state in which the second filter cover 26 is mounted on the second filter mounting part 22, the second air inlet 261 may be formed to be exposed to the outside.

The first air inlet 251 and the second air inlet 261 may be formed in the side surfaces of the first filter cover 25 and the second filter cover 26.

In some implementations, each of the first and second air inlets 251 and 261 may be formed in the front surface portion of each of the first and second filter covers 25 and 26.

The first air inlet 251 and the second air inlet 261 may be formed at a position closer to the front surface portion from a line bisecting the side surface portion.

When a plurality of first air inlets 251 is provided in the side surface portion of the first filter cover 25, a first air inlet 251 may include a first air suction hole 251a formed in the right side surface, a second air suction hole 251b formed in the left side surface and a third air suction hole 251c formed in the upper side surface.

Similarly, when a plurality of second air inlets 261 is provided in the side surface portion of the second filter cover 26, the second air inlet 261 may include a first air suction hole 261a formed in the left side surface, a second air suction hole 261b formed in the right side surface and a third air suction hole 261c formed in the upper side surface.

Meanwhile, an opening 250 may be positioned in any one of the first filter cover 25 and the second filter cover 26, or the opening 250 may be positioned in an edge of any one of the first filter cover 25 and the second filter cover 26. In addition, a manipulation part 195 configured to control operation of the mask device 1 may be mounted in the opening 250. In the present implementation, it is assumed that the manipulation part 195 is mounted on the first filter cover 25.

The manipulation part 195 may function as a manipulation switch for turning on/off the mask device 1. The manipulation part 195 may be exposed to the front side of the mask device 1 in a state of being mounted in the opening 250.

The mask body 10 may include a hook mounting part 108. The hook mounting part 108 may be provided on the left and right sides of the mask body 10. That is, the hook mounting part 108 may include a first hook mounting part 108a provided on the right side of the mask body 10 and a second hook mounting part 108b provided on the left side of the mask body 10.

A plurality of first hook mounting parts 108a and a plurality of second hook mounting parts 108b may be provided to be spaced apart from each other in the up-and-down direction of the mask body 10. Specifically, the first hook mounting part 108a may be provided on the upper right and lower right sides of the mask body 10, and the second hook mounting part 108b may be provided on the upper left and lower left sides of the mask body 10.

In the hook mounting part 108, a band for keeping the mask device 1 in close contact with the user's face may be provided.

In some examples, both ends of the band may connect the first hook mounting part 108a and the second hook mounting part 108b, wherein the band may surround the rear part of the user. In other example, both ends of the band may connect two first hook mounting parts 108a spaced apart from each other in the up-and-down direction and another band may connect two second hook mounting parts 108b spaced apart from each other in the up-and-down direction, wherein the band may be caught on both ears of the user.

The hook mounting part 108 may be formed by cutting a portion of the mask body 10. Accordingly, air may flow into an inner space between the mask body 10 and the mask body cover 20 through a gap formed in the hook mounting part 108.

Specifically, external air flowing into the inner space through the hook mounting part 108 may cool the electronic parts disposed in the inner space. In addition, temperature of the air in the inner space may rise while cooling the electronic parts and the air may be discharged to the outside of the mask body 10 through the hook mounting part 108 again. In addition, the inside of the mask device 1 may have a sealing structure in order to restrict air introduced into the inner space through the hook mounting part 108 from flowing into the breathing space.

The mask body 10 may include an air outlet 129 configured to supply filtered air to the breathing space. The user can breathe in filtered air supplied to the breathing space through the air outlet 129.

The air outlet 129 may include a first air outlet 129a configured to discharge filtered air introduced through the first air inlet 251 to the breathing space and a second air outlet 129b configured to discharge filtered air introduced through the second air inlet 261 to the breathing space.

The first air outlet 129a may be disposed on the right side of the center of the mask body 10 and the second air outlet 129b may be disposed on the left side of the center of the mask body 10. Air introduced through the first air inlet 251 may flow to the first air outlet 129a after passing through a filter 23. Air introduced through the second air inlet 261 may flow to the second air outlet 129b after passing through a filter 24.

The mask body 10 may include air outlets 154 and 155 for discharging air exhaled by the user to an outer space. The air outlets 154 and 155 may be located at the lower portion of the mask body 10.

The air outlets 154 and 155 may include a first air outlet 154 formed in the lower end of the front surface of the mask body 10 and a second air outlet 155 formed in the bottom surface of the mask body 10.

Specifically, a rib extending forward may be formed on the lower end of the front surface of the mask body 10, and a surface defined by the rib may be defined as the bottom surface of the mask body 10.

A flow space in which air passes through the first air outlet 154 and flows downward toward the second air outlet 155 may be formed between the mask body 10 and the mask body cover 20.

A check valve may be formed on at least one of the first air outlet 154 and the second air outlet 155. By using the check valve, it may be possible to prevent external air from flowing into the breathing space or prevent air discharged through the second air outlet 155 from flowing back. The check valve may be located in the flow space between the first air outlet 154 and the second air outlet 155.

For example, a check valve having a flat flap shape and corresponding in size and shape to the size and shape of the first air outlet 154 may be provided.

Specifically, the upper end of the flap may be connected to the upper edge of the first air outlet 154, such that the flap is bent or rotated to open the first air outlet 154 when a user exhales and the flap is in close contact with the first air outlet 154 to prevent external air or discharged air from flowing into the breathing space again when the user inhales.

The mask body 10 may include a sensor mounting part 109. A sensor for obtaining various types of information from the breathing space may be mounted on the sensor mounting part 109. The sensor mounting part 109 may be located at the upper portion of the mask body 10. The sensor mounting part 109 may be located at the upper portion of the mask body 10 in consideration of a location where a pressure change in the breathing space is constantly detected when the user breathes.

The mask body 10 may include a connector hole 135. The connector hole 135 may be understood as an opening in which a connector 192 for supplying power to the mask device 1 is installed. The connector hole 135 may be formed at any one of the left edge and the right edge of the mask body 10.

In the present implementation, since the manipulation part 195 and the connector are connected to a power module, the connector hole 135 may be provided on any one of the left and right sides of the mask body 10 corresponding to the position where the power module is installed.

Hereinafter, air flow during operation of the mask device will be described.

The mask device 1 according to the present disclosure may suck in external air through the air inlets 251 and 261 formed in the filter covers 25 and 26. The flow direction of the external air sucked into the mask device 1 is indicated by an arrow "A". A plurality of air inlets 251 and 261 may be configured to suck in external air in various directions, thereby increasing the amount of introduced external air.

For example, the air inlets 251 and 261 may include an upper air inlets 251a and 261a for sucking in air flowing above the filter covers 25 and 26, side air inlets 251b and 261b for sucking in air flowing at the lateral side of the filter covers 25 and 26 and a lower air inlets 251c and 261c for sucking in air flowing under the filter covers 25 and 26. The side air inlets 251b and 261b may be formed at one or both of the left and right sides of the filter covers 25 and 26.

Since the filter covers 25 and 26 in which the air inlets 251 and 261 are formed are disposed on the left and right sides of the front surface of the mask device 1, external air may be more smoothly introduced through the left and right sides of the front surface of the mask device 1.

External air introduced through the air inlets 251 and 261 may pass through the filters 23 and 24 (see FIG. 9) mounted inside the filter mounting parts 21 and 22, thereby filtering out foreign substances. The filters 23 and 24 may be replaced after separating the filter covers 25 and 26 from the mask device 1.

In some implementations, air which has passed through the filters 23 and 24 may flow into the suction port of the fan modules 16 and 17 through the air suction ports 211 and 221

(see FIG. 9). Since the filter mounting parts 21 and 22 in which the air suction ports 211 and 221 are formed and the fan modules 16 and 17 (see FIG. 9) are assembled in a state of being in close contact with each other, air which has passed through the filter may be prevented from leaking or external air may be prevented from being introduced between the filter mounting parts 21 and 22 and the fan modules 16 and 17.

Air discharged through the fan discharge port of the fan modules 16 and 17 may pass through an air duct 120 (see FIG. 9) and then flow into the breathing space S through the air outlet 129. A flow direction of air flowing into the breathing space S through the air outlet 129 is indicated by an arrow "B".

The breathing space S may be defined by the mask body 10 and the sealing part 40. When the mask body 10 is in close contact with the user's face, the sealing part 40 may be in close contact with the mask body 10 and the user's face, thereby forming an independent breathing space separate from an external space.

Air exhaled after the user breathes in filtered air supplied through the air outlet 129 may be discharged to the external space through the air outlets 154 and 155.

As described above, the air outlets 154 and 155 may include a first air outlet 154 communicating with the breathing space and a second air outlet 155 communicating with the external space, and the first air outlet 154 and the second air outlet 155 may communicate with each other by a flow space defined between the mask body 10 and the mask body cover 20. That is, air exhaled by the user is guided to the flow space through the first air outlet 154. A flow direction of air flowing to the flow space through the first air outlet 154 is indicated by an arrow "C".

Air guided to the flow space through the first air outlet 154 may be discharged to the external space through the second air outlet 155. A flow direction of air flowing to the external space through the second air outlet 155 is indicated by an arrow "D".

What is claimed is:

1. A sterilization case comprising:
a case body having a seating surface configured to seat an object to be sterilized;
a case cover that is coupled to the case body, the case cover and the case body defining an accommodation space that is configured to accommodate therein the object to be sterilized;
a sterilization module that is provided at the case body and configured to sterilize the object to be sterilized; and
a reflective pattern provided at an inner surface of the case cover and configured to reflect ultraviolet light emitted from the sterilization module onto a surface of the object to be sterilized,
wherein the reflective pattern comprises a lattice pattern or an embossed pattern formed by a plurality of protrusions protruding from the inner surface of the case cover, and
wherein a density of the plurality of protrusions defining the reflective pattern increases from an edge of the case cover to a center of the case cover.

2. The sterilization case of claim 1, wherein each of the plurality of protrusions has a transverse section of a circular or a polygonal shape.

3. A sterilization case comprising:
a case body having a seating surface configured to seat an object to be sterilized;
a case cover that is coupled to the case body, the case cover and the case body defining an accommodation space that is configured to accommodate therein the object to be sterilized;
a sterilization module that is provided at the case body and configured to sterilize the object to be sterilized; and
a reflective pattern provided at an inner surface of the case cover and configured to reflect ultraviolet light emitted from the sterilization module onto a surface of the object to be sterilized,
wherein the case cover comprises:
an outer cover having a semicircular or hemispherical shape, and
an inner cover coupled to an inner side of the outer cover, and
wherein the reflective pattern is provided at a bottom surface of the inner cover.

4. The sterilization case of claim 3, wherein at least a portion of the inner cover is coated or plated.

5. The sterilization case of claim 1, wherein the sterilization module comprises:
a first sterilization module disposed on a central portion of the seating surface;
a second sterilization module disposed on one edge of the seating surface; and
a third sterilization module disposed on another edge of the seating surface.

6. The sterilization case of claim 5, wherein the first sterilization module is configured to irradiate ultraviolet light toward a bottom surface of the object to be sterilized, and wherein the second sterilization module and the third sterilization module are configured to irradiate ultraviolet light toward a side surface of the object to be sterilized and the inner surface of the case cover.

7. The sterilization case of claim 5, wherein each of the first sterilization module, the second sterilization module, and the third sterilization module are spaced apart from the bottom surface of the case body at a same height.

8. The sterilization case of claim 5, wherein the first sterilization module, the second sterilization module, and the third sterilization module are arranged along a length direction of the case body.

9. The sterilization case of claim 5,
wherein the case body comprises:
an outer case disposed on a support surface, and
an inner case coupled to an inner side of the outer case to define the seating surface, and
wherein the seating surface is disposed on an upper surface of the inner case.

10. The sterilization case of claim 9, wherein the outer case and the inner case define a separation space that is configured to accommodate the sterilization module.

11. The sterilization case of claim 10, wherein the seating surface comprises:
a first recessed part recessed downward from the upper surface of the inner case by a predetermined depth and having an opening therein;
a pair of second recessed parts recessed downward from both ends of the first recessed part by a predetermined depth; and
a pair of third recessed parts respectively recessed downward from both ends of the pair of second recessed parts by a predetermined depth.

12. The sterilization case of claim 11, further comprising a ventilation grill provided at the opening, wherein the ventilation grill comprises:
a flat bottom portion, and a grill portion extending from an edge of the flat bottom portion to be inclined or stepped upward defining an air passage hole therein, and wherein an upper end of the grill portion is coupled to an edge of the opening.

13. The sterilization case of claim 12,
wherein the first sterilization module comprises:
a board provided at the separation space and in contact with a bottom surface of the flat bottom portion, and
a pair of light emitting diode (LED) devices disposed on the board and spaced apart from each other in a length direction of the case body, and
wherein a pair of insertion holes that accommodate the pair of LED devices is defined in the flat bottom portion.

14. The sterilization case of claim 12,
wherein a ventilation hole, configured to pass air, is defined in the outer case, and
wherein the ventilation hole is disposed below the ventilation grill.

15. The sterilization case of claim 11,
wherein the object to be sterilized comprises a mask device,
wherein the mask device comprises:
a mask body configured to cover a person's face,
a mask body cover coupled to a front surface of the mask body, and
a sealing part having a closed loop shape that is coupled to a rear surface of the mask body and configured to be in close contact with the person's face to define a breathing space therein, and
wherein both ends of the mask body cover are seated on the pair of second recessed parts.

16. The sterilization case of claim 15, wherein the first recessed part is disposed below the sealing part.

17. The sterilization case of claim 15,
wherein the second sterilization module and the third sterilization module are provided at the pair of third recessed parts, respectively,
wherein each of the second sterilization module and the third sterilization module comprises:
a board provided at the separation space and in close contact with a bottom surface of the inner case defining the pair of third recessed parts, and
a pair of LED devices disposed on the board and spaced apart from each other in a width direction of the case body, and
wherein a pair of insertion holes that accommodate the pair of LED devices is defined in the pair of third recessed parts.

18. The sterilization case of claim 12, further comprising a main control board accommodated in the separation space and disposed to surround the ventilation grill.

19. A sterilization case comprising:
a case body having a seating surface configured to seat an object to be sterilized;
a case cover that is coupled to the case body, the case cover and the case body defining an accommodation space that is configured to accommodate therein the object to be sterilized;
a sterilization module that is provided at the case body and configured to sterilize the object to be sterilized; and
a reflective pattern provided at an inner surface of the case cover and configured to reflect ultraviolet light emitted from the sterilization module onto a surface of the object to be sterilized,
wherein the sterilization module comprises:
a first sterilization module disposed on a central portion of the seating surface,
a second sterilization module disposed on one edge of the seating surface, and
a third sterilization module disposed on another edge of the seating surface,
wherein the case body comprises:
an outer case, and
an inner case coupled to an inner side of the outer case to define the seating surface,
wherein the seating surface comprises:
a first recessed part recessed downward from an upper surface of the inner case by a predetermined depth and having an opening therein,
a pair of second recessed parts recessed downward from both ends of the first recessed part by a predetermined depth, and
a pair of third recessed parts respectively recessed downward from both ends of the pair of second recessed parts by a predetermined depth,
wherein the first sterilization module is provided at the first recessed part, and
wherein the second sterilization module and the third sterilization module are provided at the pair of third recessed parts, respectively.

* * * * *